US008512727B2

(12) United States Patent
Cooper et al.

(10) Patent No.: US 8,512,727 B2
(45) Date of Patent: *Aug. 20, 2013

(54) NANOPARTICULATE MELOXICAM FORMULATIONS

(75) Inventors: Eugene R. Cooper, Berwyn, PA (US); Tuula Ryde, Malvern, PA (US); John Pruitt, Collegeville, PA (US); Laura Kline, Harleysville, PA (US)

(73) Assignee: Alkermes Pharma Ireland Limited, Dublin (IE)

( * ) Notice: Subject to any disclaimer, the term of this patent is extended or adjusted under 35 U.S.C. 154(b) by 637 days.

This patent is subject to a terminal disclaimer.

(21) Appl. No.: 10/784,900

(22) Filed: Feb. 24, 2004

(65) Prior Publication Data
US 2004/0229038 A1 Nov. 18, 2004

Related U.S. Application Data

(60) Provisional application No. 60/450,705, filed on Mar. 3, 2003.

(51) Int. Cl.
*A61F 13/00* (2006.01)
*A61K 9/14* (2006.01)

(52) U.S. Cl.
USPC .......................................... 424/422; 424/489

(58) Field of Classification Search
None
See application file for complete search history.

(56) References Cited

U.S. PATENT DOCUMENTS

| | | | |
|---|---|---|---|
| 4,233,299 A | 11/1980 | Trummlitz et al. | |
| 4,783,484 A | 11/1988 | Violante et al. | |
| 4,826,689 A | 5/1989 | Violanto et al. | |
| 4,997,454 A | 3/1991 | Violante et al. | |
| 5,133,908 A * | 7/1992 | Stainmesse et al. | 264/4.1 |
| 5,145,684 A | 9/1992 | Liversidge et al. | |
| 5,192,535 A | 3/1993 | Davis et al. | |
| 5,298,262 A | 3/1994 | Na et al. | |
| 5,302,401 A | 4/1994 | Liversidge et al. | |
| 5,318,767 A | 6/1994 | Liversidge et al. | |
| 5,326,552 A | 7/1994 | Na et al. | |
| 5,328,404 A | 7/1994 | Bacon | |
| 5,336,507 A | 8/1994 | Na et al. | |
| 5,340,564 A | 8/1994 | Illig et al. | |
| 5,346,702 A | 9/1994 | Na et al. | |
| 5,349,957 A | 9/1994 | Yudelson | |
| 5,352,459 A | 10/1994 | Hollister et al. | |
| 5,384,124 A * | 1/1995 | Courteille et al. | 424/430 |
| 5,399,363 A | 3/1995 | Liversidge et al. | |
| 5,401,492 A | 3/1995 | Kellar et al. | |
| 5,429,824 A | 7/1995 | June | |
| 5,447,710 A | 9/1995 | Na et al. | |
| 5,451,393 A | 9/1995 | Liversidge et al. | |
| 5,466,440 A | 11/1995 | Ruddy et al. | |
| 5,470,583 A | 11/1995 | Na et al. | |
| 5,472,683 A | 12/1995 | Illig | |
| 5,494,683 A | 2/1996 | Liversidge et al. | |
| 5,500,204 A | 3/1996 | Osifo | |
| 5,510,118 A * | 4/1996 | Bosch et al. | 424/489 |
| 5,518,187 A | 5/1996 | Bruno et al. | |
| 5,518,738 A | 5/1996 | Eickhoff et al. | |
| 5,521,218 A | 5/1996 | Osifo | |
| 5,525,328 A | 6/1996 | Bacon et al. | |
| 5,534,270 A | 7/1996 | De Castro | |
| 5,543,133 A | 8/1996 | Swanson et al. | |
| 5,552,160 A | 9/1996 | Liversidge et al. | |
| 5,560,931 A | 10/1996 | Eickhoff et al. | |
| 5,560,932 A | 10/1996 | Bagchi et al. | |
| 5,565,188 A | 10/1996 | Wong et al. | |
| 5,569,448 A | 10/1996 | Wong et al. | |
| 5,571,536 A | 11/1996 | Eickhoff et al. | |
| 5,573,749 A | 11/1996 | Illig | |
| 5,573,750 A | 11/1996 | Singh | |
| 5,573,783 A | 11/1996 | Desieno et al. | |
| 5,580,579 A | 12/1996 | Ruddy et al. | |
| 5,585,108 A | 12/1996 | Ruddy et al. | |
| 5,587,143 A | 12/1996 | Wong | |
| 5,591,456 A | 1/1997 | Franson et al. | |
| 5,593,097 A | 1/1997 | Corbin | |
| 5,622,938 A | 4/1997 | Wong | |
| 5,628,981 A | 5/1997 | Liversidge et al. | |
| 5,643,552 A | 7/1997 | Illig | |
| 5,662,883 A | 9/1997 | Bagchi et al. | |
| 5,665,331 A | 9/1997 | Bagchi et al. | |
| 5,718,388 A | 2/1998 | Czekai et al. | |
| 5,718,919 A | 2/1998 | Ruddy et al. | |
| 5,741,522 A | 4/1998 | Violante et al. | |
| 5,747,001 A | 5/1998 | Wiedmann et al. | |
| 5,776,496 A | 7/1998 | Violante et al. | |
| 5,834,025 A | 11/1998 | De Garavilla et al. | |

(Continued)

FOREIGN PATENT DOCUMENTS

| | | |
|---|---|---|
| CA | 2 326 517 A1 | 10/1999 |
| DE | 27 56 113 | 6/1979 |

(Continued)

OTHER PUBLICATIONS

The Physicians' Desk Reference, 56th Ed., pp. 1054 (2002).
The Merck Index, 13th Ed., pp. 1040-1041 (Merck & Co. 2001).
Lees et al., Brit. Vet. J., 147: 97 (1991).
Henderson et al., Prakt. Tierarzt., 75:179 (1994).
Tsai et al., Helv. Chim. Acta, 76:842 (1993).
Brit. J. Rheumatol., 35(Suppl. 1):1-77 (1996).
Hawkey et al., Brit. J. Rheumatol., 37:937 (1998).
Dequeker et al., Brit. J. Rheumatol., 37:946 (1998).
Vane et al., Proc. Natl. Acad. Sci. USA, 91:2046-2050 (1994).
Oulette et al., Proc. Natl. Acad. Sci., 98:14583-14588 (2001).
Seibert et al., Proc. Natl. Acad. Sci., 91:12013-12017 (1994).
Smith et al., Proc. Natl. Acad. Sci., 95:13313-13318 (1998).
Notice of Reasons for Rejections cited in related Japanese Patent Application No. 2006-532300, completed Apr. 21, 2010.
Ahmed et al., "Meloxicam in rheumatoid arthritis," pp. 739-751 (2005).

(Continued)

*Primary Examiner* — Susan Tran
(74) *Attorney, Agent, or Firm* — Foley & Lardner LLP

(57) ABSTRACT

The present invention is directed to nanoparticulate compositions comprising meloxicam. The meloxicam particles of the composition have an effective average particle size of less than about 2000 nm.

19 Claims, 1 Drawing Sheet

(56) References Cited

U.S. PATENT DOCUMENTS

| | | | |
|---|---|---|---|
| 5,861,426 A | 1/1999 | Del Soldata et al. | |
| 5,862,999 A | 1/1999 | Czekai et al. | |
| 6,045,829 A | 4/2000 | Liversidge et al. | |
| 6,068,858 A | 5/2000 | Liversidge et al. | |
| 6,153,225 A | 11/2000 | Lee et al. | |
| 6,165,506 A | 12/2000 | Jain et al. | |
| 6,184,220 B1 * | 2/2001 | Turck et al. | 514/226.5 |
| 6,221,377 B1 * | 4/2001 | Meyer | 424/434 |
| 6,221,400 B1 | 4/2001 | Liversidge et al. | |
| 6,264,922 B1 | 7/2001 | Wood et al. | |
| 6,267,989 B1 | 7/2001 | Liversidge et al. | |
| 6,270,806 B1 | 8/2001 | Liversidge et al. | |
| 6,284,269 B1 | 9/2001 | Struengmann et al. | |
| 6,316,029 B1 | 11/2001 | Jain et al. | |
| 6,375,986 B1 * | 4/2002 | Ryde et al. | 424/489 |
| 6,428,814 B1 | 8/2002 | Bosch | |
| 6,431,478 B1 | 8/2002 | Reed et al. | |
| 6,432,381 B2 | 8/2002 | Liversidge et al. | |
| 6,479,551 B1 * | 11/2002 | Plachetka et al. | 514/619 |
| 6,582,285 B2 | 6/2003 | Czekai et al. | |
| 6,592,903 B2 | 7/2003 | Ryde et al. | |
| 6,656,504 B1 | 12/2003 | Bosch et al. | |
| 6,908,626 B2 * | 6/2005 | Cooper et al. | 424/489 |
| 2002/0012675 A1 | 1/2002 | Jain et al. | |
| 2002/0019431 A1 | 2/2002 | Straub et al. | |
| 2002/0028238 A1 | 3/2002 | Karim et al. | |
| 2002/0035107 A1 | 3/2002 | Henke et al. | |
| 2002/0035264 A1 | 3/2002 | Kararli et al. | |
| 2002/0077328 A1 | 6/2002 | Hassan et al. | |
| 2003/0119825 A1 | 6/2003 | Folger et al. | |
| 2004/0018242 A1 * | 1/2004 | Cunningham et al. | 424/489 |
| 2004/0156872 A1 | 8/2004 | Bosch et al. | |
| 2006/0079516 A1 | 4/2006 | Henke et al. | |
| 2008/0132493 A1 | 6/2008 | Folger et al. | |
| 2008/0214538 A1 | 9/2008 | Bourrie et al. | |
| 2010/0137292 A1 | 6/2010 | Turp et al. | |

FOREIGN PATENT DOCUMENTS

| | | |
|---|---|---|
| EP | 0 499 299 A2 | 8/1992 |
| EP | 0 577 215 A1 | 1/1994 |
| WO | WO 93/25190 A1 | 12/1993 |
| WO | WO 9325190 A1 * | 12/1993 |
| WO | WO 96/24339 | 8/1996 |
| WO | WO 99/09988 A1 | 3/1999 |
| WO | WO 9909988 A1 * | 3/1999 |
| WO | WO 00/72973 A1 | 12/2000 |
| WO | WO 01/21154 A2 | 3/2001 |
| WO | WO 0145706 A1 * | 6/2001 |
| WO | WO 02/094215 A2 | 11/2002 |
| WO | WO 02/098565 A1 | 12/2002 |
| WO | WO 2005/105101 A1 | 11/2005 |
| WO | WO 2006/000306 A1 | 1/2006 |

OTHER PUBLICATIONS

Altman et al., "Efficacy Assessment of Meloxicam, a Preferential Cyclooxygenaise-2 Inhibitor, in Acute Coronary Syndromes without ST-Segment Elevation," 191-195 (2002).
Aoki et al., "Premedication with cyclooxygenase-2 inhibitor meloxicam reduced postoperative pain in patients after oral surgery," pp. 613-617 (2006).
Auvinet et al., "Comparison of the Onset and Intensity of Action of Intramuscular Meloxicam Oral Meloxicam in Patients with Acute Sciatica," Clin. Therap., vol. 17, No. 6, pp. 1078-1090 (1995).
Barner, "Review of Clinical Trials and Benefit/Risk Ratio of Meloxicam," pp. 29-37 (1996).
Bosch et al., "Efficacy and Tolerability of Intramuscular and Oral Meloxicam in Patents with Acute Lumbago: A Comparison with Intramuscular and Oral Piroxicam," pp. 29-38 (1997).
Busch et al., "Pharmacokinetics of Meloxicam in Animals and the Relevance to Humans," Drug Metabolism and Disposition, vol. 26, No. 6, pp. 576-584 (1998).
Busch et al., "The effect of cholestyramine on the pharmacokinetics of meloxicam, a new non-steroidal anti-inflammatory drug (NSAID), in man," pp. 269-272 (1995).

Calvo et al., "Analgesic and anti-inflammatory dose-response relationship of 7.5 and 15 mg meloxicam after lower third molar removal: a double-blind, randomized, crossover study," Int. J. Oral Maxillofac. Surg., vol. 36, pp. 26-31 (2007).
Chen et al., "Cyclooxygenase-2 selective non-steroidal anti-inflammatory drugs (etodalac, meloxicam, celecoxib, rofecoxib, etoricoxib, valdecoxib and lumiracoxib) for osteoarthritis and rheumatoid arthritis: a systematic review and economic evaluation," vol. 12, No. 11, 4 pgs. (2008).
Chung, "The Use of Injectable Nonsteroidal Anti-Inflammatory Drugs in Local Accident & Emergency Practice," Hong King Journ. of Emerg. Med., pp. 65-71 (2002).
Colberg et al., "The efficacy and tolerability of an 8-day administration of intravenous and oral meloxicam: a comparison with intramuscular and oral diclofenac in patients with acute lumbago," Current Medical Research and Opin., vol. 13, No. 7, pp. 363-377 (1996).
Combe et al., "Comparison of Intramuscular and Oral Meloxicam in Rheumatoid Arthritis Patients," pp. 10-16 (2001).
Davies et al., "Clinical Pharmacokinetics of Meloxicam," pp. 115-126 (1999).
DeAndrade et al, "Ketorolec Versus Meperidine for Pain Relief After Orthopaedic Surgery," pp. 302-312 (1996).
Degner et al., "Pharmacological, Pharmacokinetic and Clinical Profile of Meloxicam," Drugs of Today, vol. 33, No. 10, pp. 739-758 (1997).
Del Tacca et al., "Efficacy and Tolerability of Meloxicam, a COX-2 Preferential Nonsteroidal Anti-inflammatory Drug," Clin. Drug. Invest., vol. 22, No. 12, pp. 799-818 (2002).
Engelhardt, "Meloxicam Inhibits Preferentially COX-2," Euro. Journ. of Pharm., Abstracts of 4th Annual Meeting of the German Socieity of Clin. Pharmacology and Therpay, 2 pgs. (1994).
Engelhardt et al., "Anti-inflammatory, analgesic, antipyretic and related properties of meloxicam, a new non-steroidal anti-inflammatory agent with favourable gastrointestinal tolerance," Inflamm. Res., vol. 44, pp. 423-433 (1995).
Euller-Ziegler et al., "Meloxicam: a review of its pharmacokinetics, efficacy and tolerability following intramuscular administration," pp. 5-9 (2001).
Filatova et al., "Efficacy of movalis in the treatment of acute low back pains," pp. 33-37 (2005). [English Abstract].
Furst, "Meloxicam: Selective COX-2 Inhibition in Clinical Practice," pp. 21-27 (1997).
Gates et al., "Meloxicam: a reappraisal of Pharmacokinetics, efficacy and safety," pp. 2117-2140 (2005).
Gebuhr et al., "A Multiple-close, Double-blind Comparison of Intramuscularly and Orally Administered Ketorolac Tromethamine and Ketogan® in Patients with Pain Following Orthopaedic Surgery," pp. 202-217 (1994).
Ghozlan et al., "Tolerability of Multiple Administration of Intramuscular Meloxicam: A comparison with Intramuscular Piroxicam in patients with rheumatoid arthritis or osteoarthritis," pp. 51-55 (1996).
Gillis et al., "Ketorolac: A Reappraisal of its Pharmacodynamic and Pharmacokinetic Properties and Therapeutic Use in Pain Management," Drugs, vol. 53, No. 1, pp. 139-188 (1997).
Haas et al., "An Update on Analgesics for the Management of Acute Postoperative Dental Pain," Journ. of the Canadian Dental Assoc., vol. 68, No. 8, pp. 476-482 (2002).
Hawkey et al., "Gastrointestinal Tolerability of Meloxicam Compared to Diclofenac in Osteoarthritis Patients," British Society for Rheumatology, pp. 937-945 (1998).
Hill et al., "Analgesic Efficacy of the Cyclooxygenase-Inhibiting Nitric Oxide Donor AZD3582 in Postoperative Dental Pain: Comparison with Naproxen and Rofecoxib in Two Randomized, Double-Blind, Placebo-Controlled Studies," Clinical Therapeutics, vol. 28, No. 9, pp. 1279-1295 (2006).
Hinz et al., "Can Drug Removals Involving Cyclooxygenase-2 Inhibitors be Avoided? A Plea for Human Pharmacology," Trends in Pharmacological Sciences, pp. 391-397 (2008).
Hosein et al., "Evaluation of Meloxicam (a Cox-2 Inhibitor) for Management of Postoperative Endodontic Pain: A Double-blind Placebo-controlled Study," Journ. of Encodontics, pp. 634-637 (2003).

Issioui et al., "The Efficacy of Premedication with Celecoxib and Acetaminophen in Preventing Pain After Otolaryngologic Surgery," *Anesh. Analog.*, pp. 1188-1193 (2002).

Jick, "The Risk of Gastrointestinal Bleed, Myocardial Infarction and Newly Diagnosed Hypertension in Users of Meloxicam, Diclofenac, Naproxen, and Piroxicam," *Pharmacotherapy*, vol. 20, No. 7, pp. 741-744 (2000).

Kurukahvecioglu et al., "Effect of Meloxicam on Postoperative Pain Relief after Inguinal Hernia Repair with Local Anaesthesia," *West Indian Med. J.*, vol. 56, No. 6, pp. 530-533 (2007).

Lugar et al., Structure and physicochemical properties of meloxicam, a new NSAID, pp. 175-187 (1996).

Malan et al., "The Cyclooxygenase-2 Specific Inhibitor Parecoxib Sodium is as Effective as 12 mg of Morphone Administered Intramuscularly for Treating Pain After Gynecologic Laparotomy Surgery," *Anesth Analg.*, pp. 454-460 (2005).

Mazurov et al., "Use of meloxicam (movalis) in patients with rheumatic diseases with concomitant coronary heart disease," *Klin Med(Mosk)*, vol. 82, No. 12, pp. 54-59 (2004). [English Abstract].

Mitchell et al., Clinico-pharmacological studies on Ketoprofen ('Orudis'), pp. 423-430 (1975).

Naidu et al., "Physicochemical characterization and dissolution properties of meloxicam-cyclodextrin binary systems," pp. 75-86 (2004).

Narjes et al., "Pharmacokinetics and tolerability of meloxicam after i.m. administration," *Br. J. Clin. Pharm.*, vol. 41, pp. 135-139 (1996).

Nekoofar et al., "Evaluation of Meloxicam (a COX-2 Inhibitor) for Management of Postoperative Endodontic Pain: A Double-blind Placebo-controlled Study," *Journ. of Endodontics*, vol. 29, No. 10, pp. 634-637 (2003).

Nikanne et al., "Comparison of perioperative ketoprofen 2.0 mg kg-1 with 0.5 mg kg-1 i.v. in small children during adenoidectomy," *British Journ. of Anaesthesia*, vol. 79, pp. 606-608 (1997).

Odinak et al., "Use of Movalis in Treatment of Dorsophathy," 29-32 (2004). [English Abstract Included].

Palangio et al., "Combination Hydrocodone and Ibuprofen Versus Combination Oxycodone and Acetaminophen in the Treatment of Postoperative Obstetric or Gynecologic Pain," *Clin. Therapeutics*, vol. 22, No. 5, pp. 600-612 (2000).

Pallapies et al., "Effects on Platelet Functions and Pharmacokinetics of Azapropazone and Ketorolac Tromethamine Given as Single Parenteral Doses," pp. 335-339 (1993).

Panara et al., Dose-Dependent Inhibition of Platelet Cyclooxygenase-1 and Monocyte Cyclooxygenase-2 by Meloxicam in Healthy Subjects, pp. 276-280 (1999).

Power et al., "Comparison of I.M. Ketorolac Trometamol and Morphine Sulphate for Pain Relief after Cholecystectomy," British Journ. of Anaesthesia, vol. 65, pp. 448-455 (1990).

Rani et al., "Determination of Oral Meloxicam Pharmacokinetic Parameters in Asian Indians: Comparison with a German Population," *Saudi Pharm. J.*, vol. 12, No. 4, pp. 144-149 (2004).

Rao et al., "Evolution of Nonsteroidal Anti-Inflammatory Drugs (NSAIDs): Cyclooxygenase (COX) Inhibition and Beyond," *J. Pharm. Pharmaceuit Sci.*, pp. 81-110 (2008).

Rinder et al., "Effects of Meloxicam on Platelet Function in Healthy Adults: A Randomized, Double-Blind, Placebo-Controlled Trial," *J. Clin. Pharmacol.*, vol. 42, pp. 881-886 (2002).

Romsing et al., "Postoperative Analgesia is not Different After Local vs Systemic administration of Meloxicam in Patients Undergoing Inguinal Hernia Repair," *Can. J. Anesth.*, vol. 48, No. 10, pp. 978-984 (2001).

Schmid et al., "Pharmacokinetics and Metabolic Pattern after Intravenous Infusion and Oral Administration to Healthy Subjects," pp. 1206-1213 (1995).

Singh et al., "Risk of Serious Upper Gastrointestinal and Cardiovascular Thromboembolic Complications with Meloxicam," pp. 100-106 (2004).

Stei et al., Local Tissue Tolerability of Meloxicam, A New NSAID: Indications for Parenteral, Dermal and Mucosal Administration, *British Journ. of Rheumatology*, vol. 35 (Suppl. 1), pp. 44-50 (1996).

Strand, Are COX-2 Inhibitors Preferable to Non-Selective Non-Steroidal Anti-Inflammatory Drugs in Patients with Risk of Cardiovascular Events Taking Low-Dose Aspirin?, Lancet, pp. 2138-2151 (2007).

Sunshine et al., "Analgesic Efficacy of a Hydrocodone with Ibuprofen Combination Compared with Ibuprofen Alone for the Treatment of Acute Postoperative Pain," *J. Clin. Pharmacol.*, vol. 37, pp. 908-915 (1997).

Swamy et al., "Orodispersible Tablets of Meloxicam using Disintegrant Blends for Improved Efficacy," *Indian Journ. of Pharm. Sci.*, pp. 836-841 (2007).

Thompson et al., "Effect of Meloxicam on Postoperative Pain After Abdominal Hysterectomy," *British Journ. of Anaesth.*, vol. 84, No. 2, pp. 151-154 (2000).

Thwaites et al., "Intravenous Ketorolac Tromethamine Does not Worsen Platelet Function During Knee Arthroscopy Under General Anesthesia," *Anesth. Analg.*, vol. 81, pp. 119-124 (1995).

Thwaites et al., "Intravenous Ketorolac Tromethamine Worsens Platelet Function During Knee Arthroscopy Under Spinal Anesthesia," *Anesth. Analg.*, vol. 82, pp. 1176-1181 (1996).

Turck et al., "Clinical Pharmacokinetics of Meloxicam," *Arzneim.-Forsch./Drug Res.*, vol. 47(I), pp. 253-258 (1997).

Van Hecken et al., "Comparative Inhibitory Activity of Rofecoxib, Meloxicam, Diclofenac, Ibuprofen, and Naproxen on COX-2 versus COX-1 in Healthy Volunteers," *J. Clin. Pharm.*, vol. 40, pp. 1109-1120 (2000).

Van Kraaij et al., "A comparison of the effects of nabumetone vs. meloxicam on serum thromboxane $B_2$ and platelet function in healthy volunteers," pp. 644-647 (2002).

Weber et al., "COX 2 selectivity of non-steroidal anti-inflammatory drugs and perioperative blood loss in hip surgery. A randomized comparison of indoemethacin and meloxicam," pp. 963-966 (2003).

Wideman et al., "Analygesic Efficacy of a combination of hydrocodone with ibuprofen in postoperative pain," pp. 66-76 (1999).

Zelenakas et al., "Analgesic efficacy of single oral doses of lumiracoxib and ibuprofen in patients with postoperative dental pain," *J. Clin. Pract.*, vol. 58, No. 3, pp. 251-256 (2004).

Gravestock, Analytical Service Report, Meloxicam pKa and Solubility Analysis, 7 pgs., (2008).

Gravestock, Meloxicam Aq GI-Dissolution, 3 pgs. (2008).

Dreiser et al., Oral meloxicam is effective in acute sciatica: two randomised, double-blind trials versus placebo or diclofenac, *Inflamm Res.*, vol. 50, Suppl 1, pp. S17-S23 (2001).

Akarsu et al., "Preemptive meloxicam for postoperative pain relief after abdominal hysterectomy," *Clin Exp Obstet Gynecol.*, vol. 31, No. 2, pp. 133-136 (2004).

De Mello e tal., "Double-blind study to evaluate efficacy and safety of meloxicam 7.5 mg and 15 mg versus mefenamic acid 1500 mg in the treatment of primary dysmenorrheal," *Acta Obstet Gynecol Scand.*, vol. 83, No. 7, pp. 667-673 (2004).

Cheng et al., "A single-blind, randomized, controlled trial to assess the efficacy and tolerability of rofecoxib, diclofenac sodium, and meloxicam in patients with acute gouty arthritis," *Clin Ther.*, vol. 26, No. 3, pp. 399-406 (2004).

Carroll et al., "Analgesic efficacy of preoperative administration of meloxicam or butorphanol in onychectomized cats," *J. Am. Vet. Med. Assoc.*, vol. 226, No. 6, pp. 913-919 (2005).

Deneuche et al., "Analgesic comparison of meloxicam or ketoprofen for orthopedic surgery in dogs," *Vet Surg.*, vol. 33, No. 6, pp. 650-660 (2004).

Fowler et al, An evaluation of the analgesic effects of meloxicam in addition to epidural morphine/mepivacaine in dogs undergoing cranial cruciate ligament repair, *Can. Vet. J.*, vol. 44, No. 8, pp. 643-648 (2003).

Caulkett et al., A comparison of the analgesic effects of butorphanol with those of meloxicam after elective ovariohysterectomy in dogs, *Can. Vet J.*, vol. 44, No. 7, pp. 565-570 (2003).

Budsberg et al., "Evaluation of intravenous administration of meloxicam for perioperative pain management following stifle joint surgery in dogs," *Am J Vet Res.*, vol. 63, No. 11, pp. 1557-1563 (2002).

Lascelles et al., "Evaluation of the clinical efficacy of meloxicam in cats with painful locomotor disorders," *J Small Anim Pract.*, vol. 42, No. 12, pp. 587-593 (2001).

Mathews et al., "Safety and efficacy of preoperative administration of meloxicam, compared with that of ketoprofen and butorphanol in dogs undergoing abdominal surgery," *Am J Vet Res.*, vol. 62, No. 6, pp. 882-888 (2001).

Scientific Discussion, EMEA, 1-96 (2007).

International Search Report for related International Patent Application No. PCT/US2010/036304, completed Sep. 10, 2010.

Written Opinion for related International Patent Application No. PCT/US2010/036304, completed Sep. 10, 2010.

Hintz et al., "The Effect of Particle Size distribution on Dissolution Rate and Oral Absorption," *Intern. Journ. of Pharm.*, vol. 51, pp. 9-17 (1989).

Notice of Reasons for Rejection issued in related Japanese Patent Application No. 2010-233858, dated Oct. 17, 2012.

Rasenack, et al., "Micro and the Importance of Nanoparticles of Pharmacy particle size," PZ Prisma, vol. 9, No. 3, pp. 183-190 (2002).

European Office Communication cited in related European Patent Application No. 08006465.2, dated Oct. 2, 2012.

Office Action cited in related U.S. Appl. No. 12/788,203, dated Dec. 14, 2012.

Abstract only: Narjes et al., "Pharmacokinetics and Tolerability of Meloxicam after i.m. Administration," *British Journ. of Pharmacology*, vol. 41, No. 2, pp. 135-139 (1996).

Office Action cited in related U.S. Appl. No. 12/788,203, dated Apr. 11, 2012.

\* cited by examiner

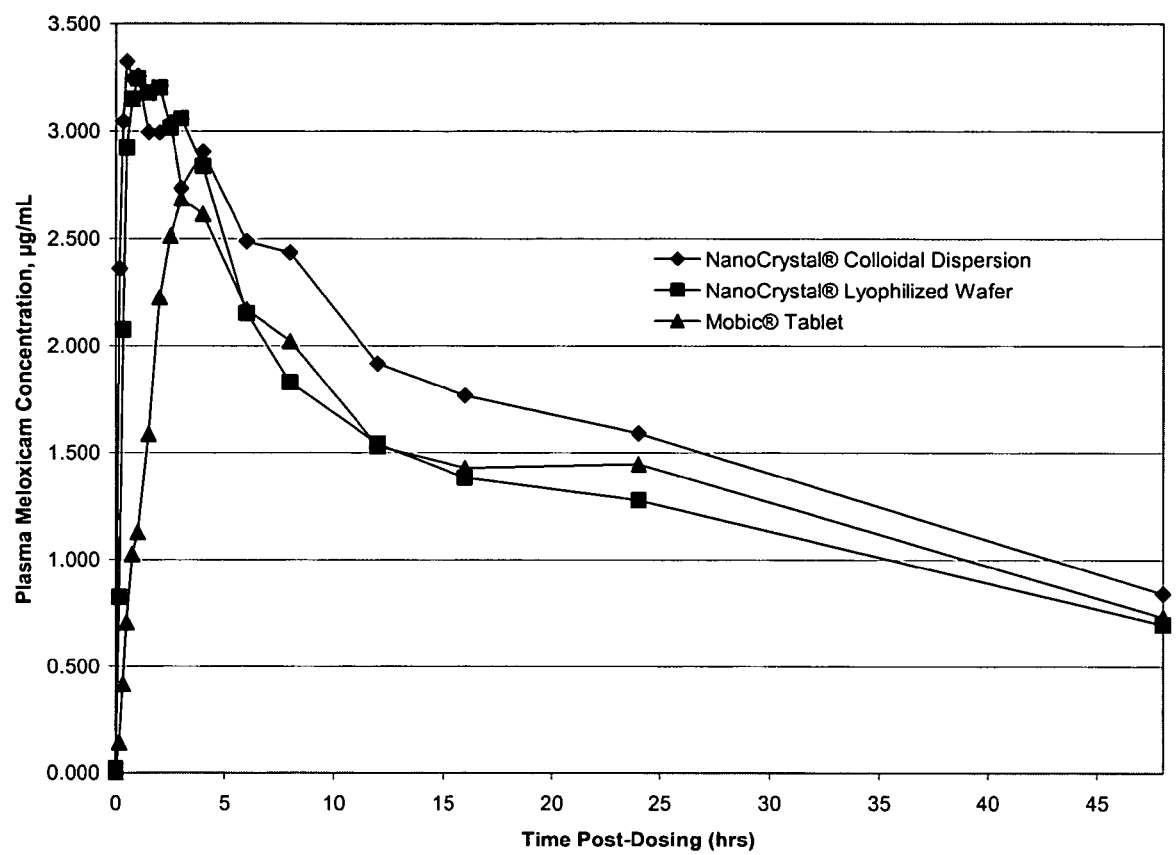

NANOPARTICULATE MELOXICAM FORMULATIONS

FIELD OF THE INVENTION

The present invention relates to nanoparticulate compositions comprising meloxicam and at least one surface stabilizer adsorbed to or associated with the surface of the drug. The nanoparticulate meloxicam particles have an effective average particle size of less than about 2000 nm.

BACKGROUND OF THE INVENTION

A. Background Regarding Nanoparticulate Active Agent Compositions

Nanoparticulate active agent compositions, first described in U.S. Pat. No. 5,145,684 ("the '684 patent"), are particles consisting of a poorly soluble therapeutic or diagnostic agent having adsorbed onto the surface thereof a non-crosslinked surface stabilizer. The '684 patent does not describe nanoparticulate compositions of meloxicam.

Methods of making nanoparticulate active agent compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate active agent compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. No. 5,399,363 and U.S. Pat. No. 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(-)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316, 029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate," U.S. Pat. No. 6,428,814 for "Bioadhesive Nanoparticulate Compositions Having Cationic Surface Stabilizers;" U.S. Pat. No. 6,431,478 for "Small Scale Mill;" U.S. Pat. No. 6,432,381 for "Methods for Targeting Drug Delivery to the Upper and/or Lower Gastrointestinal Tract," U.S. Pat. No. 6,582,285 for "Apparatus for Sanitary Wet Milling," U.S. Pat. No. 6,592,903 for "Nanoparticulate Dispersions Comprising a Synergistic Combination of a Polymeric Surface Stabilizer and Dioctyl Sodium Sulfosuccinate," and U.S. Pat. No. 6,656,504 for "Nanoparticulate Compositions Comprising Amorphous Cyclosporine and Methods of Making and Using Such Compositions," all of which are specifically incorporated by reference.

In addition, U.S. Patent Application No. 20020012675 A1, published on Jan. 31, 2002, for "Controlled Release Nanoparticulate Compositions," and WO 02/098565 for "System and Method for Milling Materials," describe nanoparticulate active agent compositions, and are specifically incorporated by reference. None of these references describe nanoparticulate compositions of meloxicam.

U.S. Patent Application No. 20020028238, published on Mar. 7, 2002, for "Use of a Celecoxib Composition for Fast Pain Relief;" U.S. Patent Application No. 20020006951, published on Jan. 17, 2002, for "Solid State Form of Celecoxib Having Enhanced Bioavailability;" and U.S. Patent Application No. 20020019431, published on Feb. 14, 2002, for "Porous Celecoxib Matrices and Methods of Manufacture Thereof," describe nanoparticulate celecoxib compositions.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter."

B. Background Regarding Meloxicam

Meloxicam, also known as 4-hydroxy-2-methyl-N-(5-methyl-2-thiazolyl)-2-H-1,2-benzothiazine-3-carboxamide 1,1-dioxide, is a member of the enolic acid group of nonsteroidal anti-inflammatory drugs (NSAIDs). Meloxicam is an oxicam derivative with the following chemical structure:

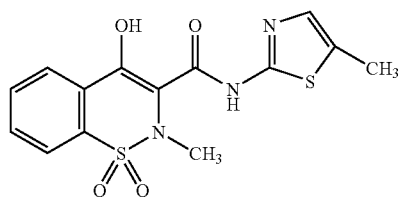 [SMILES: Cc1cnc(NC(=O)C2=C(O)c3ccccc3S(=O)(=O)N2C)s1]

Meloxicam has an empirical formula of $C_{14}H_{13}N_3O_4S_2$ and a molecular weight of 351.41. See The Physicians' Desk Reference, 56th Ed., pp. 1054 (2002); and The Merck Index, 13th Ed., pp. 1040-1041 (Merck & Co. 2001). Meloxicam is practically insoluble in water with higher solubility observed in strong acids and bases. It is very slightly soluble in methanol. The Physicians' Desk Reference, 56th Ed., pp. 1054.

4-hydroxy-2H-1,2-benzothiazine-3-carboxamide-1,1-dioxides and salts thereof, as well as methods of preparing these compounds, pharmaceutical compositions containing them as active ingredients, and methods of using them as antiphlogistics, are discussed in U.S. Pat. No. 4,233,299. See also German Patent No. 2,756,113. The pharmacology of meloxicam in horses is discussed in Lees et al., Brit. Vet. J, 147: 97 (1991); veterinary trials in dogs are discussed in Henderson et al., Prakt. Tierarzt., 75:179 (1994); the physiochemical properties of meloxicam are discussed in Tsai et al., Helv. Chim. Acta, 76:842 (1993); the pharmacology, mechanism of action, and clinical efficacy are discussed in Brit. J. Rheumatol., 35(Suppl. 1): 1-77 (1996); and clinical trials of gastrointestinal tolerability in arthritis is discussed in Hawkey et al., Brit. J. Rheumatol., 37:937 (1998), and Dequeker et al., Brit. J Rheumatol., 37:946 (1998).

Meloxicam exhibits anti-inflammatory, analgesic, and antifebrile activities. Like other NSAIDs, the primary mechanism of action of meloxicam is via inhibition of the cyclooxygenase (COX) enzyme system resulting in decreased prostaglandin synthesis. See The Physicians' Desk Reference, 56th Ed., pp. 1054 (2002). The COX enzyme system is comprised of at least two isoforms of COX. COX-1 is constituatively expressed in the gastrointestinal tract and the kidneys and is involved in the production of prostaglandins required for gastric mucosal production and proper renal blood flow. See Vane et al., Proc. Natl. Acad. Sci. USA, 91:2046-2050 (1994); Oulette et al., Proc. Natl. Acad. Sci., 98:14583-14588 (2001); and Seibert et al., Proc. Natl. Acad. Sci., 91:12013-12017 (1994). In contrast, COX-2 is not present in healthy tissue and its expression is induced in certain inflammatory states. Id.

The pathological production of prostaglandins by COX-2 is implicated in a number of human disease states, including rheumatoid arthritis, osteoarthritis, pyrexia, asthma, bone resorption, cardiovascular diseases, nephrotoxicity, atherosclerosis, and hypotension. Id. Elevated levels of prostaglandins enhance or prolong pro-inflammatory signals which cause the pain, stiffness, and inflammation associated with these conditions. See Smith et al., Proc. Natl. Acad. Sci., 95:13313-13318 (1998).

Meloxicam is superior to traditional non-selective NSAIDs because it selectively inhibits COX-2, thus causing fewer gastrointestinal problems such as bleeding, heartburn, reflux, diarrhea, nausea, and abdominal pain. Meloxicam preferentially inhibits COX-2 with a COX-2/COX-1 inhibition ratio of 0.09. It is desirable to selectively inhibit COX-2 and the pathological production of prostaglandins for which that enzyme is responsible because the therapeutic analgesic/anti-inflammatory properties of NSAIDs occur by inhibition of inducible COX-2 at the site of inflammation. Conversely, the majority of adverse drug reactions to NSAIDs, including gastrointestinal ulcers and renal failure, result from inhibition of the consitutative COX-1 enzymes. This is because as a result of such COX-1 inhibition, prostaglandins necessary for gastric mucosal production and renal blood circulation are not produced. See Vane et al., Proc. Natl. Acad. Sci. USA, 91:2046 (1994); Oulette et al., Proc. Natl. Acad. Sci., 98:14583 (2001); and Seibert et al., Proc. Natl. Acad. Sci., 91:12013 (1994). Compounds that selectively inhibit the biosynthesis of prostaglandins by inhibiting the activity of the inducible enzyme, COX-2, exert anti-inflammatory effects without the adverse side effects associated with COX-1 inhibition.

Some of the trade names under which meloxicam has or is marketed include MOBIC®, MOBEC®g), MOBICOX®, MOVALIS®, and MOVATEC®. Meloxicam has been shown to be useful in the symptomatic treatment of painful osteoarthritis (arthrosis, degenerative joint disease), symptomatic treatment of rheumatoid arthritis, symptomatic treatment of ankylosing spondylitis, and symptomatic treatment of the signs and symptoms of osteoarthritis, including pain, stiffness, and inflammation.

The form of meloxicam currently marketed in the United States is MOBIC® (Boehringer Ingelheim Pharmaceuticals, Inc., Ridgefield, Conn.), provided in 7.5 and 15 mg tablets. The bioavailability of a single 30 mg oral dose is 89% as compared to a 30 mg intravenous bolus injection. The pharmacokinetics of a single intravenous dose of meloxicam is dose-proportional in the range of 5 to 60 mg. See The Physicians' Desk Reference, 56$^{th}$ Ed., pp. 1054 (2002). After administration of multiple oral doses of meloxicam, the pharmacokinetics is dose-proportional in the range of 7.5 to 15 mg. The rate or extent of absorption is not affected by multiple dose administration. Under fasted steady state conditions, the mean $C_{max}$ is achieved within four to five hours, with a second meloxicam concentration peak occurring at approximately twelve to fourteen hours post-dose, which suggests gastrointestinal recirculation. Under steady state fed conditions in healthy adult males, the 7.5 mg tablets have a mean $C_{max}$ of 1.05 μg/mL, a $T_{max}$ of 4.9 hrs, and a $t_{1/2}$ of 20.1 hours. Under steady state fed conditions in elderly males and females, the 15 mg tablets have a $C_{max}$ of 2.3 and 3.2 μg/mL, respectively, a $T_{max}$ of 5 and 6 hrs, respectively, and a $t_{1/2}$ of 21 and 24 hrs, respectively. See The Physicians' Desk Reference, 56$^{th}$ Ed., pp. 1054 (2002).

Although meloxicam has been tested and approved by the FDA only for relief of the signs and symptoms of osteoarthritis, it may be useful in relieving the signs and symptoms of rheumatoid arthritis, lower back pain, and acute pain, e.g. treatment of post surgical pain, treatment of pain resulting from battle field wounds, and migraine headaches. Meloxicam may be especially effective for treatment of all types of pain associated with inflammation.

NSAIDs, like meloxicam, are useful in pain management because NSAIDs provide an analgesic effect without the sedation and addictive properties of narcotic analgesics. Furthermore, the long $t_{1/2}$ of meloxicam makes it useful for long-lasting relief which is not provided by narcotic analgesics. However, due to their typically long onset of action, conventional NSAIDs, including conventional meloxicam, are frequently inappropriate for management of acute pain.

Because meloxicam is practically insoluble in water, attaining sufficient bioavailability of this drug is problematic. Prior art methods of increasing the bioavailability of meloxicam include increasing its solubility by forming a cyclodextrin complex of the drug (see U.S. Pat. No. 6,284,269) or by forming a salt of meloxicam with an inorganic or organic base (U.S. Pat. Appln. Pub. No. US 2002/0035107 A1).

Published U.S. Patent Application No. 20020035264, for "Ophthalmic Formulation of a Selective Cyclooxygenase-2 Inhibitory Drug," describes pharmaceutical compositions suitable for topical administration to an eye which contain a selective COX-2 inhibitory drug, or nanoparticles of a drug of low water solubility, in a concentration effective for treatment and/or prophylaxis of a disorder in the eye, and one or more ophthalmically acceptable excipients that reduce rate of removal from the eye such that the composition has an effective residence time of about 2 to about 24 hours. Examples of such ophthalmically acceptable excipients given in the published application include cross-linked carboxyl-containing polymers which form in situ gellable aqueous solution, suspension or solution/suspension. Such excipients, which are described in U.S. Pat. No. 5,192,535, can be undesirable. Moreover, this disclosure, whis is limited to ocular formulations, does not address a need for oral fast onset meloxicam formulations for treating migraine.

Published U.S. Patent Application No. 20020077328, for "Selective Cyclooxygenase-2 Inhibitors and Vasomodulator Compounds for Generalized Pain and Headache Pain," refers to a therapeutic combination useful in the treatment, amelioration, prevention, or delay of pain comprising a high energy form of a selective cyclooxygenase-2 inhibitor, a vasomodulator, and a pharmaceutically acceptable excipient, carrier, or diluent. The cyclooxygenase-2 inhibitor and vasomodulator are each being present in an amount effective to contribute to the treatment, prevention, amelioriation or delay of pain. Disclosed vasomodulators include vasoconstrictors, vasodilators, bronchodilation agents, and bronchoconstriction agents, such as rennin-angiotensin system antagonists, nitrovasodilators, direct vasodilators, calcium channel blocking drugs, phosphodiesterase inhibitors, sympathomimetics, sympatholytics, and nitric oxide synthase inhibitors. Such additional pharmaceutical agents can be undesirable, as they can cause unwanted side-effects.

There is a need in the art to provide a readily bioavailable form of meloxicam while avoiding the prior art methods of using solubilizing agents, as well as avoiding the prior art COX-2 inhibitor formulations having undesirable qualities. The present invention satisfies this need.

There is a need in the art for nanoparticulate meloxicam formulations which overcome these and other problems associated with prior conventional meloxicam formulations. The present invention satisfies these needs.

SUMMARY OF THE INVENTION

The present invention relates to compositions comprising nanoparticulate meloxicam. The compositions comprise nanoparticulate meloxicam and at least one surface stabilizer adsorbed on or associated with the surface of the meloxicam particles. The nanoparticulate meloxicam particles, which have an effective average particle size of less than about 2000 nm, surprisingly exhibit superior $T_{max}$ profiles as compared to conventional prior meloxicam formulations.

The present invention also relates to compositions of nanoparticulate meloxicam in combination with one or more other conventional or nanoparticulate active agents. If such other active agents are in a nanoparticulate form, then such other active agents will have one or more surface stabilizers adsorbed on or associated with to the surface of the active agent. The phrase "conventional active agents or drugs," as used in this application, refers to non-nanoparticulate active agents or drugs. Non-nanoparticulate active agents have an effective average particle size of greater than about 2 microns.

Another aspect of the invention is directed to pharmaceutical compositions comprising a nanoparticulate meloxicam composition of the invention. The pharmaceutical compositions preferably comprise nanoparticulate meloxicam, at least one surface stabilizer, and a pharmaceutically acceptable carrier, as well as any desired excipients. Alternatively, such pharmaceutical compositions can additionally comprise one or more non-meloxicam conventional or nanoparticulate active agents.

The nanoparticulate meloxicam formulations of the invention may require smaller doses as compared to prior conventional meloxicam formulations. In addition, the nanoparticulate meloxicam formulations of the invention may exhibit increased bioavailability, and superior $C_{max}$ profiles as compared to conventional prior meloxicam formulations.

This invention further discloses a method of making a nanoparticulate meloxicam composition according to the invention. Such a method comprises contacting meloxicam and at least one surface stabilizer for a time and under conditions sufficient to provide a nanoparticulate meloxicam composition. The one or more surface stabilizers can be contacted with meloxicam either before, during, or after size reduction of the meloxicam. Alternatively, one or more non-meloxicam active agents can be reduced in size at the same time as meloxicam, to produce a nanoparticulate meloxican and nanoparticulate non-meloxicam active agent composition. A non-meloxicam active agent, which is either conventional or nanoparticulate sized, can also be added to the nanoparticulate meloxicam composition after size reduction.

The present invention is directed to methods of using the compositions of the invention in the treatment of, for example, pain, such as post-surgical pain, pain associated with battlefield wounds, and migraine headaches. The compositions of the invention can also be used in methods of treating the signs and symptoms of, for example, arthritis, pyrexia, asthma, bone resorption, cardiovascular diseases, nephrotoxicity, atherosclerosis, hypotension, arthrosis, ankylosing spondylitis, joint stiffness, lower back pain, pain associated with inflammation, inflammatory-related disorders, cancer, kidney disease, Alzheimer's disease, familial adenomatous polyposis, fever, acute mastitis, diarrhea, colonic adenomas, and tumors.

The compositions of the invention are useful in treating indications where anti-inflammatory agents, anti-angiogenesis agents, antitumorigenic agents, immunosuppressive agents, NSAIDs, COX-2 inhibitors, analgesic agents, antithrombotic agents, narcotics, or antifebrile agents are typically used.

Such methods comprise administering to a subject a therapeutically effective amount of a nanoparticulate meloxicam composition according to the invention. Alternatively, such methods comprise administering to a subject a therapeutically effective amount of a nanoparticulate meloxicam composition in combination with one or more non-meloxicam active agents. Such non-meloxicam active agents can be either conventional or nanoparticulate.

Both the foregoing general description and the following detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE FIGURE

FIG. 1: Shows the plasma concentration over time of meloxicam following administration of three different meloxicam formulations: a liquid dispersion of nanoparticulate meloxicam, a lyophilized wafer of nanoparticulate meloxicam, and a tablet of conventional non-nanoparticulate meloxicam, MOBIC® (Boehringer Ingelheim Pharmaceuticals, Inc.).

DETAILED DESCRIPTION OF THE INVENTION

The present invention is directed to compositions comprising nanoparticulate meloxicam. The compositions comprise nanoparticulate meloxicam and at least one surface stabilizer adsorbed on or associated with the surface of the drug. The nanoparticulate meloxicam particles, which have an effective average particle size of less than about 2000 nm, surprisingly exhibit superior $T_{max}$ profiles as compared to conventional prior meloxicam formulations.

As taught in the '684 patent, not every combination of surface stabilizer and active agent will result in a stable nanoparticulate composition. It was surprisingly discovered that stable nanoparticulate meloxicam formulations can be made. As described in more detail below, preferred surface stabilizers include polyvinylpyrrolidone (e.g., Kollidon® 12 PF, Kollidon® 17 PF), docusate sodium, block polymers of polyethylene glycol and polypropylene glycol, poloxamers (e.g., Pluronics F68® and F108®, which are block copolymers of ethylene oxide and propylene oxide), polyethylene sorbitan monooleate (Polysorbate 80), sodium Deoxycholate, lecithin, lysozyme, and mixtures thereof. Docusate sodium is particularly useful as a surface stabilizer in combination with one or more other surface stabilizers.

As described in Example 3 below, many of these surface stabilizers are particularly suited for injectable nanoparticulate meloxicam formulations. This is significant, and surprising, as for injectable formulations it is critical that very small meloxicam particles be obtained. Moreover, the composition must be stable, with very little or no particle size growth observed, as injectable formulations having large particles can cause embolism.

Nanoparticulate meloxicam formulations suitable parenteral injection (e.g., intravenous, intramuscular, or subcutaneous) for the treatment of acute pain are highly superior to conventional meloxicam formulations because they have much faster onset of action due to the nanoparticulate size of the active agent.

In addition to exhibiting dramatically superior $T_{max}$ profiles, the nanoparticulate meloxicam formulations preferably also exhibit improved pharmacokinetic profiles as compared to conventional meloxicam formulations, resulting in faster onset of action and smaller effective doses as compared to prior conventional meloxicam formulations.

Conventional formulations of meloxicam are inappropriate for management of acute pain due to delayed onset of action, as such meloxicam formulations have a $T_{max}$ of 4-6 hours, which is more than five times as long as most narcotic analgesic drugs. See The Physician's Desk Reference, 56$^{th}$ Ed., pp. 446 and 1054. Unlike conventional meloxicam formulations, nanoparticulate meloxicam formulations, which exhibit faster onset of action, are useful in treating acute pain where fast pain relief is required.

Additionally, any drug, including meloxicam, can have adverse side effects. Thus, lower doses of meloxicam which can achieve the same or better therapeutic effects as those observed with larger doses of conventional meloxicam are desired.

Nanoparticulate formulations of meloxicam also provide a longer duration of pain relief as compared to traditional narcotic analgesic drugs. While traditional narcotics provide fast onset of action, the duration of pain relief is short. Nanoparticulate meloxicam formulations combine the fast onset of traditional narcotics with the duration of pain relief of conventional NSAIDs. The long half-life of meloxicam, approximately 20 hours as compared to 2-3 hours for most narcotics, confers a long duration of action and thus requires less frequent dosing.

Additionally, nanoparticulate meloxicam formulations do not possess the sedative and addictive properties of narcotic analgesics. Meloxicam does not cause drowsiness and is not addictive, making it a preferred analgesic when ambulation is important or when treatment is protracted and chemical dependency could result from continued use of narcotic analgesics.

Nanoparticulate formulations can be prepared for oral administration for treatment of, for example, migraine headaches. The use of oral nanoparticulate formulations also provide much faster onset of action as compared to conventional orally dosed meloxicam formulations.

In addition, the invention encompasses compositions comprising nanoparticulate meloxicam, one or more surface stabilizers, and one or more non-meloxicam active agents, either conventional or nanoparticulate. Methods of using such combination compositions are also encompassed by the invention. For example, additional analgesic drugs can be used in combination with nanoparticulate meloxicam, such as one or more COX-2 inhibitors, NSAIDs, or narcotics. Other exemplary types of active agents which can be used in combination with nanoparticulate meloxicam are described below. If the non-meloxicam active agent is in nanoparticulate form, then such a non-meloxicam active agent also has one or more surface stabilizers adsorbed on or associated with the surface of the active agent. The surface stabilizer(s) adsorbed on or associated with the surface of the non-meloxicam active agent can be the same as or different from the surface stabilizer(s) adsorbed on or associated with the surface of the nanoparticulate meloxicam.

In general, such non-meloxicam active agents do not include vasomodulators, such as those described in U.S. Published Patent Application No. 20020077328.

In yet another embodiment of the invention, a first meloxicam formulation providing the pharmacokinetic profile required herein is co-administered with at least one other meloxicam formulation that generates a different pharmacokinetic profile, specifically one exhibiting slower absorption into the bloodstream and therefore a longer $T_{max}$, and typically a lower $C_{max}$. For example, the second meloxicam formulation can have a conventional particle size, which produces a longer $T_{max}$, and typically a lower $C_{max}$. Alternatively, a second, third, or fourth meloxicam formulation can differ from the first, and from each other, in the effective average particle sizes of each composition. The different particle sizes produce different $T_{maxs}$. The combination of fast pain relief provided by the first formulation and longer-lasting pain relief provided by the second (or third, fourth, etc.) formulation can reduce the dose frequency required.

Preferably where co-administration of a "fast-acting" formulation and a "longer-lasting" formulation is desired, the two formulations are combined within a single composition, for example a dual-release composition.

A. Compositions

The invention provides compositions comprising nanoparticulate meloxicam particles and at least one surface stabilizer. The surface stabilizers are adsorbed on or associated with the surface of the meloxicam particles. Surface stabilizers useful herein physically adhere on the surface of the nanoparticulate meloxicam but do not chemically react with the meloxicam particles or itself. Individual molecules of the surface stabilizer are essentially free of intermolecular cross-linkages.

The invention also provides compositions of nanoparticulate meloxicam in combination with one or more conventional or nanoparticulate non-meloxicam drugs.

The present invention includes nanoparticulate meloxicam compositions together with one or more non-toxic physiologically acceptable carriers, adjuvants, or vehicles, collectively referred to as carriers. The compositions can be formulated for parenteral injection (e.g., intravenous, intramuscular, or subcutaneous), oral (in solid, liquid, or aerosol form), vaginal, nasal, rectal, ocular, local (powders, ointments or drops), buccal, intracisternal, intraperitoneal, or topical administration, and the like. Such compositions can also comprise one or more conventional or nanoparticulate non-meloxicam drugs.

The present invention provides compositions of meloxicam with a desirable pharmacokinetic profile when administered to mammalian subjects. Preferably, the $T_{max}$ of a 7.5 mg orally administered dose of nanoparticulate meloxicam, when assayed in the plasma of a mammalian subject following administration of an initial dose, is less than about 5 hours, less than about 4 hours, less than about 3 hours, less than about 2 hours, less than about 1 hour, less than less than about 50 minutes, less than about 45 minutes, less than about 40 minutes, less than about 35 minutes, less than about 30 minutes, less than about 20 minutes, less than about 15 minutes, less than about 10 minutes, or less than about 5 minutes.

In addition, preferably the $C_{max}$ of a 7.5 mg orally administered dose of nanoparticulate meloxicam, when assayed in the plasma of a mammalian subject following administration of an initial dose, is greater than about 1 µg/mL, greater than about 3 µg/mL, greater than about 5 µg/mL, greater than about 10 µg/mL, or greater than about 15 µg/mL.

The desirable pharmacokinetic profile, as used herein, is the pharmacokinetic profile measured after the initial dose of meloxicam. The compositions can be formulated in any way as described below.

A preferred nanoparticulate meloxicam formulation of the invention exhibits in comparative pharmacokinetic testing with a standard commercial formulation of meloxicam, such as MOBIC® from Boehringer Ingelheim Pharmaceuticals, Inc., a $T_{max}$ not greater than about 90%, not greater than about 80%, not greater than about 70%, not greater than about 60%, not greater than about 50%, not greater than about 30%, not greater than about 25%, not greater than about 20%, not greater than about 15%, or not greater than about 10% of the $T_{max}$ exhibited by a standard commercial meloxicam formulation, e.g., MOBIC® tablets.

In addition, a preferred nanoparticulate meloxicam formulation of the invention exhibits in comparative pharmacokinetic testing with a standard commercial formulation of meloxicam, such as MOBIC® from Boehringer Ingelheim Pharmaceuticals, Inc., a $C_{max}$ which is greater than about 20%, greater than about 40%, greater than about 60%, greater than about 80%, greater than about 100%, greater than about 140%, greater than about 180%, greater than about 200%, greater than about 240%, greater than about 280%, greater than about 300%, greater than about 340%, greater than about 380%, or greater than about 400% of the $C_{max}$ exhibited by a standard commercial meloxicam formulation, e.g., MOBIC® capsules.

Any nanoparticulate meloxicam formulation giving the desired pharmacokinetic profile is suitable for administration according to the present methods.

1. Meloxicam Particles

As used herein the term meloxicam, which is the active ingredient in the composition, is used to mean meloxicam (4-hydroxy-2-methyl-N-(5-methyl-2-thiazolyl)-2-H-1,2-benzothiazine-3-carboxamide 1,1-dioxide) or any salt thereof. Meloxicam can be present in a crystalline phase, an amorphous phase, a semi-crystalline phase, a semi-amorphous phase, or a mixture thereof.

Nanoparticulate meloxicam compositions are contemplated to be useful in treatment and/or prevention of a wide range of conditions and disorders mediated by COX-2, including but not limited to, disorders characterized by inflammation, pain, and/or fever. Such compositions are especially useful as anti-inflammatory agents, such as in treatment of arthritis, with the additional benefit of having significantly less harmful side effects than compositions of conventional NSAIDs that lack selectivity for COX-2 over COX-1. In particular, such compositions have reduced potential for gastrointestinal toxicity and gastrointestinal irritation including upper gastrointestinal ulceration and bleeding, reduced potential for renal side effects such as reduction in renal function leading to fluid retention and exacerbation of hypertension, reduced effect on bleeding times including inhibition of platelet function, and possibly a lessened ability to induce asthma attacks in aspirin-sensitive asthmatic subjects, by comparison with compositions of conventional NSAIDs.

Thus, nanoparticulate meloxicam compositions of the invention are particularly useful as an alternative to conventional NSAIDs where such NSAIDs are contraindicated, for example in patients with peptic ulcers, gastritis, regional enteritis, ulcerative colitis, diverticulitis, or with a recurrent history of gastrointestinal lesions; gastrointestinal bleeding; coagulation disorders including anemia such as hypoprothrombinemia, hemophilia, or other bleeding problems; kidney disease; or in patients prior to surgery or patients taking anticoagulants.

Because of the rapid onset of therapeutic effect observed with the compositions of the invention, these compositions have particular advantages over prior conventional formulations for treatment of acute COX-2 mediated disorders, especially for relief of pain, for example in headache, including sinus headache and migraine.

Meloxicam is also useful in treating and/or preventing, for example, arthritic disorders, gastrointestinal conditions, inflammatory conditions, pulmonary inflammation, opthalmic diseases, central nervous systems disorders, pain, inflammation-related cardiovascular disorders, angiogenesis-related disorders, benign and malignant tumors, adenomatous polyps, disorders of the female reproductive system such as endometriosis, osteoporosis, dysmenorrhea, premature labor, asthma, eosinophil-related disorders, pyrexia, bone resorption, nephrotoxicity, hypotension, arthrosis, joint stiffness, kidney disease, liver disease including hepatitis, acute mastitis, diarrhea, colonic adenomas, bronchitis, allergic neuritis, cytomegalovirus infectivity, apoptosis including HIV-induced apoptosis, lumbago; skin-related conditions such as psoriasis, eczema, acne, burns, dermatitis, and ultraviolet radiation damage including sunburn; allergic rhinitis, respiratory distress syndrome, and endotoxin shock syndrome. Nanoparticulate meloxicam is also useful as an immunosuppressive agent.

Exemplary forms of arthritic disorders which can be treated include, but are not limited to, osteoarthritis, rheumatoid arthritis, spondyloarthropathies, gouty arthritis, juvenile arthritis, gout, ankylosing spondylitis, systemic lupus erythematosus, bursitis, tendinitis, myofascial pain, carpal tunnel syndrome, fibromyalgia syndrome, infectious arthritis, psoriatic arthritis, reiter's syndrome, and scleroderma Exemplary gastrointestinal conditions or ulcerative diseases which can be treated include, but are not limited to, inflammatory bowel disease, Crohn's disease, gastritis, irritable bowel syndrome, ulcerative colitis, gastric ulcer, pathological but non-malignant conditions such as hemangiomas, including infantile hemaginomas, angiofibroma of the nasopharynx, and avascular necrosis of bone.

Exemplary inflammation conditions which can be treated include, but are not limited to, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, postoperative inflammation including that following ophthalmic surgery such as cataract surgery or refractive surgery, and the like.

Exemplary pulmonary inflammation conditions which can be treated include, but are not limited to, inflammation associated with viral infections and cystic fibrosis, and in bone resorption such as that associated with osteoporosis.

Exemplary opthalmic diseases or conditions which can be treated include, but are not limited to, retinitis, conjunctivitis, retinopathies, uveitis, ocular photophobia, acute injury to the eye tissue, corneal graft rejection, ocular neovascularization, retinal neovascularization including neovascularization following injury or infection, diabetic retinopathy, macular degeneration, retrolental fibroplasia, glaucoma, and neovascular glaucoma.

Exemplary central nervous system disorders which can be treated include, but are not limited to, cortical dementias including Alzheimer's disease, neurodegeneration, and central nervous system damage resulting from stroke, ischemia, and trauma. The term "treatment" in the present context includes partial or total inhibition of dementias, including Alzheimer's disease, vascular dementia, multi-infarct dementia, pre-senile dementia, alcoholic dementia, and senile dementia.

Exemplary pain conditions which can be treated include, but are not limited to, postoperative pain, pain resulting from battle field wounds, dental pain, muscular pain, pain resulting from cancer, headaches, including sinus headache and migraine, menstrual cramps, and pain associated with inflammation.

The compositions of the invention are useful for relief of pain, fever, and inflammation in a variety of conditions including rheumatic fever, influenza, and other viral infections including common cold, low back, and neck pain, dysmenorrhea, headache, toothache, sprains and strains, myositis, neuralgia, synovitis, arthritis, including rheumatoid arthritis, degenerative joint diseases (osteoarthritis), gout, ankylosing spondylitis, bursitis, burns, and trauma following surgical and dental procedures.

Exemplary inflammation-related cardiovascular disorders which can be treated or prevented using the compositions of the invention include, but are not limited to, vascular diseases, coronary artery disease, aneurysm, vascular rejection, arteriosclerosis, atherosclerosis including cardiac transplant atherosclerosis, myocardial infarction, embolism, stroke, thrombosis including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins, and capillaries. Exemplary angiogenesis-related disorders include, but are not limited to, inhibition of tumor angiogenesis. Such compositions are useful in treatment of neoplasia, including metastasis, benign and malignant tumors, and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers that effect epithelial cells throughout the body. Neoplasias for which compositions of the invention are contemplated to be particularly useful are gastrointestinal cancer, Barrett's esophagus, liver cancer, bladder cancer, pancreatic cancer, ovarian cancer, prostate cancer, cervical cancer, lung cancer, breast cancer and skin cancer. The nanoparticulate meloxicam compositions of the invention can also be used to treat fibrosis that occurs with radiation therapy.

The compositions of the invention can be used to treat subjects having adenomatous polyps, including those with familial adenomatous polyposis (FAP). Additionally, such compositions can be used to prevent polyps from forming in patients at risk of FAP.

Because the meloxicam compositions of the invention inhibit prostanoid-induced smooth muscle contraction by inhibiting synthesis of contractile prostanoids, the compositions can be used in the treatment of dysmenorrhea, premature labor, asthma, and eosinophil-related disorders.

The compositions of the invention are also useful in treating indications where anti-inflammatory agents, anti-angiogenesis agents, antitumorigenic agents, immunosuppressive agents, NSAIDs, COX-2 inhibitors, analgesic agents, antithrombotic agents, narcotics, or antifebrile agents are typically used.

2. Non-Meloxicam Active Agents

The nanoparticulate meloxicam compositions of the invention can additionally comprise one or more non-meloxicam active agents, in either a conventional or nanoparticulate form. The non-meloxicam active agents can be present in a crystalline phase, an amorphous phase, a semi-crystalline phase, a semi-amorphous phase, or a mixture thereof.

If the non-meloxicam active agent is in a nanoparticulate form, then it will have one or more surface stabilizers adsorbed on or associated with the surface of the active agent. In addition, if the active agent is in a nanoparticulate form it is preferably poorly soluble, and is dispersible in at least one liquid dispersion medium. By "poorly soluble" it is meant that the active agent has a solubility in a liquid dispersion medium of less than about 10 mg/mL, and preferably less than about 1 mg/mL. Useful liquid dispersion mediums include, but are not limited to, water, aqueous salt solutions, safflower oil, and solvents such as ethanol, t-butanol, hexane, and glycol.

Such active agents can be, for example, an active, therapeutic, or diagnostic agent. A therapeutic agent can be a pharmaceutical agent, including biologics such as proteins, peptides, and nucleotides, or a diagnostic agent, such as a contrast agent, including x-ray contrast agents. The active agent can be selected from a variety of known classes of drugs, including, for example, proteins, peptides, nucleotides, anti-obesity drugs, nutraceuticals, dietary supplements, carotenoids, corticosteroids, elastase inhibitors, antifungals, oncology therapies, anti-emetics, analgesics, cardiovascular agents, anti-inflammatory agents, such as NSAIDs and COX-2 inhibitors, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

A description of these classes of active agents and a listing of species within each class can be found in Martindale's *The Extra Pharmacopoeia,* 31$^{st}$ Edition (The Pharmaceutical Press, London, 1996), specifically incorporated by reference. The active agents are commercially available and/or can be prepared by techniques known in the art.

Exemplary nutraceuticals and dietary supplements are disclosed, for example, in Roberts et al., *Nutraceuticals: The Complete Encyclopedia of Supplements, Herbs, Vitamins, and Healing Foods* (American Nutraceutical Association, 2001), which is specifically incorporated by reference. A nutraceutical or dietary supplement, also known as phytochemicals or functional foods, is generally any one of a class of dietary supplements, vitamins, minerals, herbs, or healing foods that have medical or pharmaceutical effects on the body. Exemplary nutraceuticals or dietary supplements include, but are not limited to, lutein, folic acid, fatty acids (e.g., DHA and ARA), fruit and vegetable extracts, vitamin and mineral supplements, phosphatidylserine, lipoic acid, melatonin, glucosamine/chondroitin, Aloe Vera, Guggul, glutamine, amino acids (e.g., iso-leucine, leucine, lysine, methionine, phenylanine, threonine, tryptophan, and valine), green tea, lycopene, whole foods, food additives, herbs, phytonutrients, antioxidants, flavonoid constituents of fruits, evening primrose oil, flax seeds, fish and marine animal oils, and probiotics. Nutraceuticals and dietary supplements also include bio-engineered foods genetically engineered to have a desired property, also known as "pharmafoods."

Nanoparticulate meloxican compositions useful in methods of the present invention can be used in combination therapies with opioids and other analgesics, including narcotic analgesics, Mu receptor antagonists, Kappa receptor antagonists, non-narcotic (i.e., non-addictive) analgesics, monoamine uptake inhibitors, adenosine regulating agents, cannabinoid derivatives, Substance P antagonists, neurokinin-1 receptor antagonists and sodium channel blockers, among others.

Preferred combination therapies comprise a composition useful in methods of the invention with one or more compounds selected from aceclofenac, acemetacin, e-acetamidocaproic acid, acetaminophen, acetaminosalol, acetanilide, acetylsalicylic acid (aspirin), S-adenosylmethionine, alclofenac, alfentanil, allylprodine, alminoprofen, aloxiprin, alphaprodine, aluminum bis(acetylsalicylate), amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antipyrine salicylate, antrafenine, apazone, bendazac, benorylate, benoxaprofen, benzpiperylon, benzydamine, benzylmorphine, bermoprofen, bezitramide, -bisabolol, bromfenac, p-bromoacetanilide, 5-bromosalicylic acid acetate, bromosaligenin, bucetin, bucloxic acid, bucolome, bufexamac, bumadizon, buprenorphine, butacetin, butibufen, butophanol, calcium acetylsalicylate, carbamazepine, carbiphene, carprofen, carsalam, chlorobutanol, chlorthenoxazin, choline salicylate, cinchophen, cinmetacin, ciramadol, clidanac, clometacin, clonitazene, clonixin, clopirac, clove, codeine, codeine methyl bromide, codeine phosphate, codeine sulfate, cropropamide, crotethamide, desomorphine, dexoxadrol, dextromoramide, dezocine, diampromide, diclofenac sodium, difenamizole, difenpiramide, diflunisal, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, flufenamic acid, flunoxaprofen, fluoresone, flupirtine, fluproquazone, flurbiprofen, fosfosal, gentisic acid, glafenine, glucametacin, glycol salicylate, guaiazulene, hydrocodone, hydromorphone, hydroxypethidine, ibufenac, ibuprofen, ibuproxam, imidazole salicylate, indomethacin, indoprofen, isofezolac, isoladol, isomethadone, isonixin, isoxepac, isoxicam, ketobemidone, ketoprofen, ketorolac, p-lactophenetide, lefetamine, levorphanol, lofentanil, lonazolac, lomoxicam, loxoprofen, lysine acetylsalicylate, magnesium acetylsalicylate, meclofenamic acid, mefenamic acid, meperidine, meptazinol, mesalamine, metazocine, methadone hydrochloride, methotrimeprazine, metiazinic acid, metofoline, metopon, mofebutazone, mofezolac, morazone, morphine, morphine hydrochloride, morphine sulfate, morpholine salicylate, myrophine, nabumetone, nalbuphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paranyline, parsalmide, pentazocine, perisoxal, phenacetin, phenadoxone, phenazocine, phenazopyridine hydrochloride, phenocoll, phenoperidine, phenopyrazone, phenyl acetylsalicylate, phenylbutazone, phenyl salicylate, phenyramidol, piketoprofen, piminodine, pipebuzone, piperylone, piprofen, pirazolac, piritramide, piroxicam, pranoprofen, proglumetacin, proheptazine, promedol, propacetamol, propiram, propoxyphene, propyphenazone, proquazone, protizinic acid, ramifenazone, remifentanil, rimazolium metilsulfate, salacetamide, salicin, salicylamide, salicylamide o-acetic acid, salicylsulfuric acid, salsalte, salverine, simetride, sodium salicylate, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tolfenamic acid, tolmetin, tramadol, tropesin, viminol, xenbucin, ximoprofen, zaltoprofen, and zomepirac. See The Merck Index, 12th Edition (1996), Therapeutic Category and Biological Activity Index, lists therein headed "Analgesic", "Anti-inflammatory", and "Antipyretic").

Particularly preferred combination therapies comprise use of a nanoparticulate meloxicam composition of the invention with an opioid compound, more particularly where the opioid compound is codeine, meperidine, morphine, or a derivative thereof.

The compound to be administered in combination with a nanoparticulate meloxicam composition of the invention can be formulated separately from said composition or co-formulated with said composition. Where a meloxicam composition is co-formulated with a second drug, for example an opioid drug, the second drug can be formulated in immediate-release, rapid-onset, sustained-release, or dual-release form.

In an embodiment of the invention, particularly where the COX-2 mediated condition is headache or migraine, the nanoparticulate meloxicam composition is administered in combination therapy with a vasomodulator, preferably a xanthine derivative having vasomodulatory effect, more preferably an alkylxanthine compound.

Combination therapies wherein an alkylxanthine compound is co-administered with a nanoparticulate meloxicam composition as provided herein are embraced by the present embodiment of the invention whether or not the alkylxanthine is a vasomodulator and whether or not the therapeutic effectiveness of the combination is to any degree attributable to a vasomodulatory effect. The term "alkylxanthine" herein embraces xanthine derivatives having one or more $C_1$-4 alkyl substituents, preferably methyl, and pharmaceutically acceptable salts of such xanthine derivatives. Dimethylxanthines and trimethylxanthines, including caffeine, theobromine, and theophylline, are especially preferred. Most preferably, the alkylxanthine compound is caffeine.

Exemplary COX-2 inhibitors which can be formulated in combination with the nanoparticulate meloxicam composition of the invention include, but are not limited to, celecoxib, rofecoxib (Vioxx®), meloxicam (MOBIC®, co-marketed by Abbott Laboratories, Chicago, Ill., and Boehringer Ingelheim Pharmaceuticals, Inc.), valdecoxib (G.D. Searle & Co.), parecoxib (G.D. Searle & Co.), MK-966 (Merck, in Phase III studies), etoricoxib (MK-663; Merck, in Phase II studies), SC-236 (chemical name of 4-[5-(4-chlorophenyl)-3-(trifluoromethyl)-1H-pyrazol-1-yl)] benzenesulfonamide; G.D. Searle & Co., Skokie, Ill.); NS-398 (N-(2-cyclohexyloxy-4-nitrophenyl)methane sulfonamide; Taisho Pharmaceutical Co., Ltd., Japan); SC-58125 (methyl sulfone spiro(2.4)hept-5-ene I; Pharmacia/Searle & Co.); SC-57666 (Pharmacia/Searle & Co.); SC-58635 (celexcoxib; Pharmacia/Searle & Co.); SC-558 (Pharmacia/Searle & Co.); SC-560 (Pharmacia/Searle & Co.); etodolac (Lodine®, Wyeth-Ayerst Laboratories, Inc.); DFU (5,5-dimethyl-3-(3-fluorophenyl)-4-(4-methylsulfonyl)phenyl 2(5H)-furanone); MK-476, L-745337, L-761066, L-761000, L-748780, and L-748731 (all Merck & Co.); DUP-697 (5-Bromo-2-(4-fluorophenyl)-3-(4-(methylsulfonyl)phenyl; DuPont Merck Pharmaceutical Co.); PGV 20229 (1-(7-tert.-butyl-2,3-dihydro-3,3-dimethylbenzo(b)furan-5-yl)-4-cyclopropylbutan-1-one) (Procter & Gamble Pharmaceuticals); T-614 (3-formylamino-7-methylsulfonylamino-6-phenoxy-4H-1-benzopyran-4-one;
Toyama Corp., Japan); BF 389 (Biofor, USA); PD 136005, PD 142893, and PD 145065 (all Parke-Davis/Warner-Lambert Co.); flurbiprofen (Ansaid®; Pharmacia & Upjohn); nimesulide (NIM-03, Mesulid®; Hisamitsu, Japan); nabumetone (Relafen®; SmithKline Beecham, plc); flosulide (CGP 28238; Novartis/Ciba Geigy); piroxicam (Feldene®; Pfizer); dicofenac (Voltaren® and Cataflam®, Novartis); COX-189 (Novartis); D 1367 (Celltech Chiroscience, plc); R 805 (4 nitro 2 phenoxymethane sulfonanilide); R 807 (3 benzoyldifluoromethane sulfonanilide, diflumidone); JTE-522 (Japan Tobacco, Japan); FK-3311 (4'-Acetyl-2'-(2,4-difluorophenoxy)methanesulfonanilide; Fujisawa, Japan); FK 867 (Fujisawa, Japan); FR 115068 (Fujisawa, Japan); GR 253035 (Glaxo Wellcome); RWJ 63556 (Johnson & Johnson); RWJ 20485 (Johnson & Johnson); ZK 38997 (Schering); S 2474 ((E)-(5)-(3,5-di-tert-butyl-4-hydroxybenzylidene)-2-ethyl-1,2-isothiazolidine-1,1-dioxide indomethacin; Shionogi & Co., Ltd., Japan); CL 1004 (Parke-Davis); RS 57067 (Hoffmann La Roche); RS 104894 (Hoffmann La Roche); SC 41930 (Monsanto); SB 205312 (SmithKline Beecham); SKB 209670 (SmithKline Beecham, plc); and Ono 1078 (Ono Pharmaceutical Co., Japan).

3. Surface Stabilizers

The choice of one or more surface stabilizers for meloxicam is non-trivial and required extensive experimentation to realize a desirable formulation. Accordingly, the present invention is directed to the surprising discovery that nanoparticulate meloxicam compositions can be made.

Combinations of more than one surface stabilizer can be used in the invention. Useful surface stabilizers which can be employed in the invention include, but are not limited to, known organic and inorganic pharmaceutical excipients. Such excipients include various polymers, low molecular weight oligomers, natural products, and surfactants. Preferred surface stabilizers include nonionic, cationic, and ionic surfactants.

Representative examples of surface stabilizers include hydroxypropyl methylcellulose, hydroxypropylcellulose, polyvinylpyrrolidone, sodium lauryl sulfate, dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3550® and 934' (Union Carbide)), polyoxyethylene stearates, colloidal silicon dioxide, phosphates, carboxymethylcellulose calcium, carboxymethylcellulose sodium, methylcellulose, hydroxyethylcellulose, hydroxypropylmethylcellulose phthalate, noncrystalline cellulose, magnesium aluminium silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508, a poloxamine) (BASF Wyandotte Corporation), Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-10G® or Surfactant 10-G® (Olin Chemicals, Stamford, Conn.); Crodestas SL-40® (Croda, Inc.); and SA9OHCO, which is $C_{18}H_{37}CH_2C(O)N(CH_3)-CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate, and the like.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($C_{12-18}$)dimethylbenzyl ammonium chloride, N-alkyl ($C_{14-18}$) dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™ (polyquatemium 10; Buckman Laboratories, TN), tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ (quaternized ammonium salt polymers) and ALKAQUAT™ (benzalkonium chloride) (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly [diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Nonpolymeric surface stabilizers are any nonpolymeric compound, such benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$:
(i) none of $R_1$-$R_4$ are $CH_3$;
(ii) one of $R_1$-$R_4$ is $CH_3$;
(iii) three of $R_1$-$R_4$ are $CH_3$;
(iv) all of $R_1$-$R_4$ are $CH_3$;
(v) two of $R_1$-$R_4$ are $CH_3$, one of $R_1$-$R_4$ is $C_6H_5CH_2$, and one of $R_1$-$R_4$ is an alkyl chain of seven carbon atoms or less;
(vi) two of $R_1$-$R_4$ are $CH_3$, one of $R_1$-$R_4$ is $C_6H_5CH_2$, and one of $R_1$-$R_4$ is an alkyl chain of nineteen carbon atoms or more;
(vii) two of $R_1$-$R_4$ are $CH_3$ and one of $R_1$-$R_4$ is the group $C_6H_5(CH_2)_n$, where n>1;
(viii) two of $R_1$-$R_4$ are $CH_3$, one of $R_1$-$R_4$ is $C_6H_5CH_2$, and one of $R_1$-$R_4$ comprises at least one heteroatom;
(ix) two of $R_1$-$R_4$ are $CH_3$, one of $R_1$-$R_4$ is $C_6H_5CH_2$, and one of $R_1$-$R_4$ comprises at least one halogen;
(x) two of $R_1$-$R_4$ are $CH_3$, one of $R_1$-$R_4$ is $C_6H_5CH_2$, and one of $R_1$-$R_4$ comprises at least one cyclic fragment;
(xi) two of $R_1$-$R_4$ are $CH_3$ and one of $R_1$-$R_4$ is a phenyl ring; or
(xii) two of $R_1$-$R_4$ are $CH_3$ and two of $R_1$-$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference.

The surface stabilizers are commercially available and/or can be prepared by techniques known in the art.

4. Other Pharmaceutical Excipients

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™).

Suitable lubricants, including agents that act on the flowability of a powder to be compressed, are colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, mint flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

5. Nanoparticulate Meloxicam and Active Agent Particle Size

The compositions of the invention comprise meloxicam nanoparticles which have an effective average particle size of less than about 2000 nm (i.e., 2 microns), less than about 1500 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

If the composition additionally comprises one or more non-meloxicam nanoparticulate active agents, then such active agents have an effective average particle size of less than about 2000 nm (i.e., 2 microns), less than about 1500 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

By "an effective average particle size of less than about 2000 nm" it is meant that at least 50% of the meloxicam or nanoparticulate active agent particles have a particle size of less than about 2000 nm when measured by the above-noted techniques. Preferably, at least 70%, 90%, or 95% of the meloxicam particles have a particle size of less than the desired particle size, e.g., 2000 nm, 1500 nm, 1000 nm, etc.

6. Concentration of Nanoparticulate Meloxicam, Surface Stabilizers, and Optional One or More Active Agents The relative amounts of meloxicam and one or more surface stabilizers can vary widely. The optimal amount of the individual components can depend, for example, upon the particular active agent selected, the hydrophilic lipophilic balance (HLB), melting point, and the surface tension of water solutions of the stabilizer, etc.

The concentration of meloxicam can vary from about 99.5% to about 0.001%, from about 95% to about 0.1%, and from about 90% to about 0.5%, by weight, based on the total combined weight of the meloxicam and at least one surface stabilizer, not including other excipients.

The concentration of the at least one surface stabilizer can vary from about 0.01% to about 99.5%, from about 0.1% to about 95%, and from about 0.5% to about 90%, by weight, based on the total combined dry weight of the meloxicam and at least one surface stabilizer, not including other excipients.

B. Methods of Making Nanoparticulate Formulations

The nanoparticulate meloxicam compositions can be made using, for example, milling, homogenization, or precipitation techniques. Exemplary methods of making nanoparticulate compositions are described in the '684 patent. Methods of making nanoparticulate compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference.

One or more non-meloxicam active agents can also be reduced in size at the same time as meloxicam, to produce a nanoparticulate meloxican and nanoparticulate non-meloxicam active agent composition. A non-meloxicam active agent, which is either conventional or nanoparticulate sized, can also be added to the nanoparticulate meloxicam composition after size reduction.

In yet another embodiment of the invention, nanoparticulate meloxicam compositions of the invention can be made in which the formulation comprises multiple nanoparticulate meloxicam compositions, each of which has a different effective average particle size. Such a composition can be made by preparing the individual nanoparticulate meloxicam formulations using, for example, milling, precipitation, or homogenization techniques, followed by combining the different compositions to prepare a single dosage form.

1. Milling to Obtain Nanoparticulate Meloxicam Dispersions

Milling meloxicam to obtain a nanoparticulate dispersion comprises dispersing meloxicam particles in a liquid dispersion medium in which meloxicam is poorly soluble, followed by applying mechanical means in the presence of rigid grinding media to reduce the particle size of meloxicam to the desired effective average particle size. The dispersion medium can be, for example, water, safflower oil, ethanol, t-butanol, glycerin, polyethylene glycol (PEG), hexane, or glycol.

The meloxicam particles can be reduced in size in the presence of at least one surface stabilizer. Alternatively, the meloxicam particles can be contacted with one or more surface stabilizers after attrition. Other compounds, such as a diluent, can be added to the meloxicam/surface stabilizer composition during the size reduction process. Dispersions can be manufactured continuously or in a batch mode. The resultant nanoparticulate meloxicam dispersion can be utilized in solid or liquid dosage formulations, such as liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc.

2. Precipitation to Obtain Nanoparticulate Meloxicam Compositions

Another method of forming the desired nanoparticulate meloxicam composition is by microprecipitation. This is a method of preparing stable dispersions of poorly soluble active agents in the presence of one or more surface stabilizers and one or more colloid stability enhancing surface active agents free of any trace toxic solvents or solubilized heavy metal impurities. Such a method comprises, for example: (1) dissolving meloxicam in a suitable solvent; (2) adding the formulation from step (1) to a solution comprising at least one surface stabilizer; and (3) precipitating the formulation from step (2) using an appropriate non-solvent. The method can be followed by removal of any formed salt, if present, by dialysis or diafiltration and concentration of the dispersion by conventional means. The resultant nanoparticulate meloxicam dispersion can be utilized in solid or liquid dosage formulations, such as liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc.

3. Homogenization to Obtain Meloxicam Nanoparticulate Compositions

Exemplary homogenization methods of preparing active agent nanoparticulate compositions are described in U.S. Pat. No. 5,510,118, for "Process of Preparing Therapeutic Compositions Containing Nanoparticles." Such a method comprises dispersing meloxicain particles in a liquid dispersion medium, followed by subjecting the dispersion to homogenization to reduce the particle size of the meloxicam to the desired effective average particle size. The meloxicam particles can be reduced in size in the presence of at least one surface stabilizer. Alternatively, the meloxicam particles can be contacted with one or more surface stabilizers either before or after attrition. Other compounds, such as a diluent, can be added to the meloxicam/surface stabilizer composition either before, during, or after the size reduction process. Dispersions can be manufactured continuously or in a batch mode. The resultant nanoparticulate meloxicam dispersion can be utilized in solid or liquid dosage formulations, such as liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc.

C. Methods of Using Meloxicam Formulations of the Current Invention

The meloxicam compositions of the present invention can be administered to a subject via any conventional means including, but not limited to, orally, rectally, ocularly, parenterally (e.g., intravenous, intramuscular, or subcutaneous), intracisternally, pulmonary, intravaginally, intraperitoneally, locally (e.g., powders, ointments or drops), or as a buccal or nasal spray. As used herein, the term "subject" is used to mean an animal, preferably a mammal, including a human or non-human. The terms patient and subject may be used interchangeably.

The present invention provides a method of rapidly increasing the plasma levels of meloxicam in a subject. Such a method comprises administering to a subject an effective amount of a composition comprising nanoparticulate meloxicam.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include, but are not limited to, capsules, tablets, pills, powders, and granules. In such solid dosage forms, the active agent is admixed with at least one of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active agent, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Ocular dosage forms of the nanoparticulate meloxicam of the invention preferably do not include cross-linked carboxyl-containing polymers, used as excipients, as described in U.S. Pat. No. 5,192,535. Such excipients can be undesirable.

One of ordinary skill will appreciate that effective amounts of meloxicam can be determined empirically and can be employed in pure form or, where such forms exist, in pharmaceutically acceptable salt, ester, or prodrug form. Actual dosage levels of meloxicam in the nanoparticulate compositions of the invention may be varied to obtain an amount of meloxicam that is effective to obtain a desired therapeutic response for a particular composition and method of administration. The selected dosage level therefore depends upon the desired therapeutic effect, the route of administration, the potency of the administered meloxicam, the desired duration of treatment, and other factors.

Dosage unit compositions may contain such amounts of such submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

1. Use of Additional Active Agents

The methods of the invention also encompass administering a nanoparticulate meloxicam composition of the invention in combination with one or more non-meloxicam active agents, in either a conventional or nanoparticulate form. In general, such additional active agents do not include vasomodulators, such as those described in U.S. Published Application No. 2002007328.

2. Treatment Applications

The compositions of the invention are useful in treating and/or preventing, for example, conditions in which NSAIDs are contraindicated, arthritic disorders, gastrointestinal conditions, inflammatory conditions, pulmonary inflammation, opthalmic diseases, central nervous systems disorders, pain, fever, inflammation-related cardiovascular disorders, angiogenesis-related disorders, benign and malignant tumors, adenomatous polyps, fibrosis which occurs with radiation treatment, disorders of the female reproductive system such as endometriosis, osteoporosis, dysmenorrhea, premature labor, asthma, eosinophil-related disorders, pyrexia, bone resorption, nephrotoxicity, hypotension, arthrosis, joint stiffness, kidney disease, liver disease including hepatitis, acute mastitis, diarrhea, colonic adenomas, bronchitis, allergic neuritis, cytomegalovirus infectivity, apoptosis including HIV-induced apoptosis, lumbago, skin-related conditions such as psoriasis, eczema, acne, burns, dermatitis, and ultraviolet radiation damage including sunburn, allergic rhinitis, respiratory distress syndrome, and endotoxin shock syndrome. Nanoparticulate meloxicam is also useful as an immunosuppressive agent.

The compositions of the invention are also useful in treating indications where anti-inflammatory agents, anti-angiogenesis agents, antitumorigenic agents, immunosuppressive agents, NSAIDs, COX-2 inhibitors, analgesic agents, antithrombotic agents, narcotics, or antifebrile agents are typically used.

More detailed descriptions of the arthritis disease conditions osteoarthritis and rheumatoid arthritis are given below.

3. Arthritis

Although the term "arthritis" literally means joint inflammation, arthritis refers to a group of more than 100 rheumatic diseases and conditions that can cause pain, stiffness, and swelling in the joints. Certain conditions may affect other parts of the body, such as the muscles, bones, and some internal organs, and can result in debilitating, and sometimes life-threatening, complications. If left undiagnosed and untreated, arthritis can cause irreversible damage to the joints.

Arthritis already affects more than 42 million Americans in its chronic form, including 300,000 children. By 2020, the Center for Disease Control estimates that 60 million people will be affected, and that more than 11 million will be disabled. See http://www.fda.gov/fdac/features/2000/300_arth.html. The two most common forms of the disease, osteoarthritis and rheumatoid arthritis, have the greatest public health implications, according to the Arthritis Foundation. Id. Other common forms arthritis and related conditions include juvenile arthritis, gout, ankylosing spondylitis, systemic lupus erythematosus, bursitis, tendinitis and myofascial pain, carpal tunnel syndrome, fibromyalgia syndrome, infectious arthritis, psoriatic arthritis, reiter's syndrome, and scleroderma.

Osteoarthritis, previously known as "degenerative joint disease," results from wear and tear on the joints, like the knees, hips and fingers, or from an injury. The pressure of gravity causes physical damage to the joints and surrounding tissues, leading to pain, tenderness, swelling, and decreased function. Initially, osteoarthritis is non-inflammatory and its onset is subtle and gradual, usually involving one or only a few joints. Pain is the earliest symptom, usually made worse by repetitive use. Risk factors for osteoarthritis include aging, joint trauma, obesity, repetitive joint use, and diabetes.

Many people may have only mild discomfort with osteoarthritis. But as cartilage covering the ends of bones in the joints wears away, considerable pain, inflammation, and loss of movement can result. Osteoarthritis affects all parts of a joint, causing pain and stiffness, especially after physical activity.

Osteoarthritis affects more than 20 million people, and the risk of getting it increases with age. It is the most common joint disease. About one-third of people over age 35 show some signs of osteoarthritis when they have x-rays. The joints most often affected are the knee, hip, and hand. In people over age 55, osteoarthritis of the hip is more common in men and osteoarthritis of the fingers is more common in women. Osteoarthritis of the knees causes problems for both men and women. In the United States, about 100,000 people can't walk from their beds to their bathrooms without help because of osteoarthritis of the knee or hip.

Rheumatoid arthritis is an autoimmune disease that occurs when the body's own immune system mistakenly attacks the synovium (cell lining inside the joint). This chronic, potentially disabling disease causes pain, stiffness, swelling, and loss of function in the joints. Rheumatoid arthritis affects about one in every 100 people. It affects women three times more often than men. The people most likely to develop rheumatoid arthritis are those between the ages of 35 and 50.

Rheumatoid arthritis affects the joint membranes, cartilage, and bones the way osteoarthritis does. But unlike osteoarthritis, rheumatoid arthritis can also affect the whole body, with loss of appetite, a general feeling of being unwell, and other symptoms. The exact cause of rheumatoid arthritis is unknown, although it may be triggered by the immune system (the body's defenses) turning against the body.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

EXAMPLE 1

The purpose of this example is describe how a nanoparticle dispersion of meloxicam could be prepared.

A desired quantity of meloxicam and at least one surface stabilizer can be milled in the presence of suitable rigid grinding media for a suitable period of time in, for example, a DYNO®-Mill KDL (Willy A. Bachofen AG, Maschinenfabrik, Basel, Switzerland), a roller mill (U.S. Stoneware), or a NanoMill® (Elan Drug Delivery Inc.) (see e.g., WO 00/72973 for "Small-Scale Mill and Method Thereof").

The mean particle size of the resultant compositions, as measured using, for example, a Horiba LA-910 Laser Scattering Particle Size Distribution Analyzer (Horiba Instruments, Irvine, Calif.) is expected to be less than 2 microns. The dispersion is expected to exhibit excellent stability over an extended period of time over a range of temperatures.

EXAMPLE 2

The purpose of this example is to describe how a solid dose form of nanoparticulate meloxicam could be prepared.

The nanoparticulate dispersion of Example 1 can be spray dried, lyophilized, or spray granulated to form a powder. The resulting powder or granules of nanoparticulate meloxicam can then be mixed with the suitable excipients, such as the ingredients listed in Table 1, followed by tableting.

TABLE 1

| Ingredient Description | Percent of Total (Per Tablet) |
|---|---|
| Nanoparticulate Meloxicam Spray Dried Powder | 50.2 |
| Pregelatinized Starch NF (Colorcon ® Starch 1500) | 20.0 |
| Microcrystalline Cellulose NF (Avicel ® PH101) | 20.0 |
| Sodium Starch Glycorlate (Explotab ®) | 5.3 |
| Croscarmellose Sodium USP (Ac-Di-Sol ®) | 4.0 |
| Magnesium Stearate NF | 0.5 |
| Totals | 100.0 |

The tablets are expected to show excellent redispersion in water as well as in simulated biological fluids. This is significant as redispersion in simulated biological fluids is predictive of redispersion under in vivo conditions.

EXAMPLE 3

The purpose of this example was to prepare nanoparticulate dispersions of meloxicam stabilized with various surface modifiers intended for injectable administration.

Aqueous dispersions of 5 wt. % meloxicam (Unichem Laboratories, Ltd.) and 1 wt. % stabilizer (see Table 2, below) were charged into a NanoMill® milling system (Elan Drug Delivery, Inc., King of Prussia, Pa.; see e.g., U.S. Pat. No. 6,431,478 for "Small Scale Mill") equipped with a 10 cc batch chamber.

The following NanoMill® milling system parameters were used for all of the formulations: mill speed=5500 rpm; total milling time=1 hour; polymeric milling media type=polyMil™-200 (The Dow Chemical Co.); and a media load sufficient to process.

Particle size analysis of the resultant milled dispersions was performed using a Horiba LA-910 particle size analyzer ((Horiba Instruments, Irvine, Calif.). The results are shown below in Table 2. In the table below, the value for D50 is the particle size below which 50% of the active agent particles fall. Similarly, D90 is the particle size below which 90% of the active agent particles fall.

TABLE 2

| Stabilizer | Stabilizer Manufacturer | Mean (nm) | D50 (nm) | D90 (nm) | Optical Microscopy* |
|---|---|---|---|---|---|
| Pluronic ® F68 (poloxamer 188) | BASF | 133 | 110 | 226 | Stable |
| Pluronic ® F108 (poloxamer 388) | BASF | 129 | 108 | 219 | Stable |
| Kollidon ® 12 PF | BASF | 98 | 90 | 125 | Stable |
| Kollidon ® 17 PF | BASF | 98 | 95 | 135 | Stable |
| Polysorbate 80 | Spectrum | 227 | 227 | 322 | Stable |
| Sodium Deoxycholate | Prodotti Chimici | 119 | 101 | 198 | Stable |
| Lecithin | Penta | 190 | 169 | 271 | Mild aggregation at initial |
| Lysozyme | Fordras | 95 | 89 | 117 | Moderate aggregation at initial; Stable at 24 hours |

*All formulations were taken at initial time except for Lethicin and Lysozyme, wherein the initial particle size was measured at 24 hr.

The results demonstrate that meloxicam can be formulated into stable nanoparticulate compositions suitable for IV administration with each of the surface stabilizers shown in Table 2, as all of the formulations have a particle size suitable for injectable compositions. Nanoparticulate compositions shown in Table 2 had mean particles sizes ranging from 95 to 227 nm, with D50 and D90 sizes ranging from 89 nm to 227 nm and 117 nm to 322 nm, respectively.

EXAMPLE 4

The purpose of this example was to test in vivo the nanoparticulate meloxicam compositions of the invention.

Four male and four female Beagle dogs were fasted overnight. In addition, each dog was fasted for four (4) hours post dose. Each dog received three different meloxicam formualtions, which are described in more detail below. Formulation #1 was a liquid dispersion of nanoparticulate meloxicam particles; Formulation #2 was a lyophilized table of nanoparticulate meloxicam particles; and Formulation #3 was a MOBIC® 7.5 mg Tablet (Boehringer Ingelheim Pharmaceuticals, Inc.).

Summary of Formulations Used in the Protocol
Formulation # 1. (Liquid Dispersion)

8.0 g meloxicam (Unichem Laboratories, Ltd.) was added to a solution containing 1.6 g F127 NF Lutrol® (BASF) and 70.4 g water. Lutrol® F127, also known as Poloxamer 407, is a block polymer consisting of 73% of polyethylene glycol and 27% polypropylene glycol. This mixture was then milled in a DYNO®-Mill KDL (Willy A. Bachofen AG, Maschinenfabrik, Basel, Switzerland) at 4200 RPM with PolyMill®-500 polymeric media for 160 minutes. The mean (weight average) final meloxicam particle size was 111 nm, as measured on a Horiba LB-910 particle size analyzer (Horiba Instruments, Irvine, Calif.).

5 grams of the meloxicam dispersion was then added to 45 grams of water to give a final concentration of 1% meloxicam.
Formulation # 2 (Lyophilzed Wafers)

A "fast melt" lyophilized dosage form was prepared from a nanoparticulate dispersion of meloxicam to see how the lyophilization and reconstitution process affected the pharmacokinetic data.

8.0 g meloxicam (Unichem Laboratories, Ltd.) was added to a solution containing 2.4 g polyvinylpyrrolidone (PVP) Plasdoneg K29/32 (ISP Technologies), 1.6 g docusate sodium (Cytec), and 68 g water. This mixture was then milled in a DYNO-Mill KDL (Willy A. Bachofen AG, Maschinenfabrik, Basel, Switzerland) at 4200 RPM with PolyMill®-500 polymeric media for 150 minutes.

The mean particle size of the meloxicam dispersion following milling was 101 nm, as measured on a Horiba LA-910 particle size analyzer.

1.5 grams of the dispersion was then added to 4.0 grams Mannitol USP/NF (Specturm), 1.2 grams Pullulan (Hayashibara), 0.8 grams Glycerol USP (Spectrum), and 32.5 grams of water.

A wafer tray was then filled by adding 2 grams of the diluted dispersion to each 2.5 cc well and the wafer tray was then placed in a lyophilizer for 48 hours to produce the final lyophilized wafer dosage form.

The meloxicam particle size in the lyophilized wafers appears stable. After 2.5 months the reconstituted mean particle size of the meloxicam particles was 111 nm.
Formulation # 3 (Tablet)
MOBIC® Tablets (Boehringer Ingelheim), 7.5 mg.

Dog Study Protocol

In Phase 1, each dog received a single oral gavage dose of 7.5 mg meloxicam (0.75 ml of a 10 mg/ml Formulation #1), followed by an approximately 10 mL tap water flush of the gavage tube.

In Phase 2, after a 7-day washout period, the same eight dogs received a 7.5 mg dose of meloxicam as a single lyophilized wafer (Formulation #2).

In Phase 3, after a 7-day washout period, the same 8 dogs received a single 7.5 mg tablet of MOBIC® (lot # 251586N) (Formulation #3).

Results

Blood samples were collected and processed to plasma at the conclusion of each phase as follows: Blood samples (approximately 1 mL) were drawn at specified time points into tubes containing potassium EDTA (blood collected predose and at 0.167, 0.333, 0.5, 0.75, 1, 1.5, 2, 2.5, 3, 4, 6, 8, 12, 16, 24, and 48 hours postdose). The samples were placed on wet ice following collection. Plasma was separated and stored frozen in tubes containing potassium EDTA at approximately −20° C. until shipped to the Sponsor-designated laboratory. The $C_{max}$, $T_{max}$, and AUC for the three different formulations is shown below in Table 3.

TABLE 4

| Formulation | Cmax (µg/mL) | Tmax (hours) | AUC |
|---|---|---|---|
| 1 (liquid dispersion) | 3.499 | 0.750 | 118.225 |
| 2 (lyophilized wafer) | 3.420 | 1.292 | 106.642 |
| 3 (MOBIC ®) | 2.768 | 3.375 | 99.870 |

Both the liquid dispersion of nanoparticulate meloxicam (Formulation #1) and the lyophilized wafer of nanoparticulate meloxicam (Formulation #2) showed a faster onset time and a larger $C_{max}$ than the commercial MOBIC® tablet. In addition, the smaller particle sizes of the nanoparticulate meloxicam formulations resulted in faster dissolution, thereby producting a much shorter $T_{max}$ (0.75 and 1.3 hours, respectively, for Formulations #1 and #2, as compared to 3.4 hours for Formulation #3). See FIG. 1.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. An intravenous injection pharmaceutical dosage form comprising:
   (a) a liquid dispersion medium selected from the group consisting of water, an aqueous salt solution, safflower oil, ethanol, t-butanol, hexane and glycol;
   (b) particles of meloxicam or a salt thereof having an effective average particle size of less than 200 nm; and
   (c) polyvinylpyrrolidone and sodium deoxycholate as surface stabilizers adsorbed on the surface of the meloxicam particles,
   wherein:
   (i) the surface stabilizer are essentially free of intermolecular cross-linkages;
   (ii) meloxicam is present in an amount of from about 99.5% to about 0.001%, by weight, based on the total combined weight of the meloxicam and the surface stabilizers; and
   (iii) the surface stabilizers are present in an amount of from about 0.01% to about 99.5%, by weight, based on the total combined weight of the meloxicam and the surface stabilizers.

2. The pharmaceutical dosage form of claim 1, wherein the meloxicam is selected from the group consisting of a crystalline phase, an amorphous phase, and a semi-crystalline phase.

3. The pharmaceutical dosage form of claim 1, wherein the effective average particle size of the meloxicam particles is selected from the group consisting of less than 100 nm, less than 75 nm, and less than 50 nm.

4. The pharmaceutical dosage form of claim 1, wherein the pharmaceutical dosage form further comprises one or more pharmaceutically acceptable excipients, carriers, or a combination thereof.

5. A method of making an intravenous injection pharmaceutical dosage form comprising contacting meloxicam particles with polyvinylpyrrolidone and sodium deoxycholate as surface stabilizers in the presence of a liquid dispersion medium selected from the group consisting of water, an aqueous salt solution, safflower oil, ethanol, t-butanol, hexane and glycol for a time and under conditions sufficient to provide the intravenous injection pharmaceutical dosage form comprising meloxicam particles having an effective average particle size of less than 200 nm, wherein:
   (i) the surface stabilizers are essentially free of intermolecular cross-linkages;
   (ii) meloxicam is present in an amount of from about 99.5% to about 0.001%, by weight, based on the total combined weight of the meloxicam and the surface stabilizers; and
   (iii) the surface stabilizers are present in an amount of from about 0.01% to about 99.5%, by weight, based on the total combined weight of the meloxicam and the surface stabilizers.

6. The method of claim 5, wherein said contacting comprises grinding.

7. The method of claim 6, wherein said grinding comprises wet grinding.

8. The method of claim 5, wherein said contacting comprises homogenizing.

9. The method of claim 5, wherein said contacting comprises:
   (a) dissolving the meloxicam particles in a solvent;
   (b) adding the resulting meloxicam solution to a solution comprising at least one surface stabilizer; and
   (c) precipitating the solubilized meloxicam having at least one surface stabilizer associated with the surface thereof by the addition thereto of a non-solvent.

10. The method of claim 5, wherein the meloxicam is selected from the group consisting of a crystalline phase, an amorphous phase, and a semi-crystalline phase.

11. The method of claim 5, wherein the effective average particle size of the nanoparticulate meloxicam particles is selected from the group consisting of less than 100 nm, less than 75 nm, and less than 50 nm.

12. The method of claim 5, wherein the pharmaceutical dosage form further comprises one or more pharmaceutically acceptable excipients, carriers, or a combination thereof.

13. A method of treating a subject in need thereof comprising intravenously injecting to the subject an effective amount of a pharmaceutical dosage form comprising:
   (a) a liquid dispersion medium selected from the group consisting of water, an aqueous salt solution, safflower oil, ethanol, t-butanol, hexane and glycol;
   (b) particles of meloxicam or a salt thereof; and
   (c) polyvinylpyrrolidone and sodium deoxycholate as surface stabilizers,
   wherein:
   (i) the surface stabilizers are essentially free of intermolecular cross-linkages;
   (ii) the meloxicam particles have an effective average particle size of less than 200 nm;
   (iii) meloxicam is present in an amount of from about 99.5% to about 0.001, by weight, based on the total combined weight of the meloxicam and the surface stabilizers; and
   (iv) the surface stabilizer is present in an amount of from about 0.01% to about 99.5%, by weight, based on the total combined dry weight of meloxicam and the surface stabilizers.

14. The method of claim 13, wherein the meloxicam is selected from the group consisting of crystalline phase, an amorphous phase, and a semi-crystalline phase.

15. The method of claim 13, wherein the effective average particle size of the nanoparticulate meloxicam particles is selected from the group consisting of less than 100 nm, less than 75 nm, and less than 50 nm.

16. The method of claim 13, wherein the pharmaceutical dosage form further comprises one or more pharmaceutically acceptable excipients, carriers, or a combination thereof.

17. The method of claim 13, wherein the method is used to treat a condition selected from the group consisting of conditions in which NSAIDs are contraindicated, arthritic disorders, gastrointestinal conditions, inflammatory conditions, pulmonary inflammation, opthalmic diseases, central nervous systems disorders, pain, fever, inflammation-related cardiovascular disorders, angiogenesis-related disorders, benign tumors, malignant tumors, adenomatous polyps, endometriosis, osteoporosis, dysmenorrhea, premature labor, asthma, fibrosis which occurs with radiation treatment, eosinophil-related disorders, pyrexia, bone resorption, nephrotoxicity, hypotension, arthrosis, joint stiffness, kidney disease, liver disease, acute mastitis, diarrhea, colonic adenomas, bronchitis, allergic neuritis, cytomegalovirus infectivity, apoptosis, lumbago, psoriasis, eczema, acne, burns, dermatitis, ultraviolet radiation damage, allergic rhinitis, respiratory distress syndrome, and endotoxin shock syndrome.

18. The method of claim 13, wherein the method is used to treat an indication in which anti-inflammatory agents, anti-angiogenesis agents, antitumorigenic agents, immunosuppressive agents, NSAIDs, COX-2 inhibitors, analgesic agents, anti-thrombotic agents, narcotics, or antifebrile agents are typically used.

19. The method of claim 13, wherein said subject is a human.

* * * * *